: United States Patent  
Blain et al.

(10) Patent No.: US 8,888,820 B2  
(45) Date of Patent: Nov. 18, 2014

(54) SPINAL STABILIZATION DEVICE

(75) Inventors: Jason Blain, Encinitas, CA (US); Gregory Martin, Encinitas, CA (US); Matthew Lake, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 1414 days.

(21) Appl. No.: 12/147,159

(22) Filed: Jun. 26, 2008

(65) Prior Publication Data

US 2009/0082819 A1     Mar. 26, 2009

Related U.S. Application Data

(60) Provisional application No. 60/946,893, filed on Jun. 28, 2007.

(51) Int. Cl.
| | | |
|---|---|---|
| A61B 17/70 | (2006.01) | |
| A61B 17/04 | (2006.01) | |
| A61B 17/86 | (2006.01) | |
| A61F 2/08 | (2006.01) | |

(52) U.S. Cl.
CPC ......... *A61B 17/7037* (2013.01); *A61B 17/7032* (2013.01)
USPC ............ 606/270; 606/268; 606/274; 606/306

(58) Field of Classification Search
CPC .................................................. A61B 17/7037
USPC .................. 606/264–275, 305–306, 308, 310
See application file for complete search history.

(56) References Cited

U.S. PATENT DOCUMENTS

| | | | |
|---|---|---|---|
| 5,207,678 A | | 5/1993 | Harms et al. |
| 5,474,555 A | | 12/1995 | Puno et al. |
| 5,565,565 A | | 10/1996 | Lodewijk et al. |
| 5,885,286 A | * | 3/1999 | Sherman et al. ............ 606/270 |
| RE37,665 E | | 4/2002 | Ralph et al. |
| 6,458,132 B2 | * | 10/2002 | Choi ............................ 606/267 |
| 6,554,834 B1 | | 4/2003 | Crozet et al. |
| 6,565,565 B1 | | 5/2003 | Yuan et al. |
| 6,755,829 B1 | | 6/2004 | Bono et al. |
| RE39,089 E | | 5/2006 | Ralph et al. |

(Continued)

FOREIGN PATENT DOCUMENTS

| | | |
|---|---|---|
| DE | 44 33 360 | 2/1996 |
| WO | WO 2005/087120 | 9/2005 |
| WO | WO 2007/041265 | 4/2007 |

OTHER PUBLICATIONS

PCT/US08/868393 International Search Report dated Jan. 5, 2009.

(Continued)

*Primary Examiner* — Andrew Iwamaye
(74) *Attorney, Agent, or Firm* — Knobbe, Martins, Olson & Bear, LLP

(57) ABSTRACT

A bone attachment device comprises an attachment collar having a hinged lid is disclosed. The bone attachment device may also comprise a bone fastener (such as a bone screw). A bone attachment device including an attachment collar and a spinal rod locking device is disclosed. A bone attachment device as described herein may be used together with a spinal stabilization rod and one or more additional bone attachment devices. Such devices are adapted to clamp and hold a spinal stabilization rod. Methods for implanting a spinal stabilizer having a bone attachment device including a hinged lid are disclosed.

14 Claims, 15 Drawing Sheets

(56) References Cited

U.S. PATENT DOCUMENTS

| | | |
|---|---|---|
| 7,087,057 B2 | 8/2006 | Konieczynski et al. |
| 7,125,426 B2 | 10/2006 | Moumene et al. |
| 7,141,051 B2 | 11/2006 | Janowski et al. |
| 7,144,396 B2 | 12/2006 | Shluzas |
| 7,811,310 B2* | 10/2010 | Baker et al. .................. 606/267 |
| 2003/0050640 A1* | 3/2003 | Lee et al. ...................... 606/61 |
| 2003/0125742 A1* | 7/2003 | Yuan et al. .................... 606/61 |
| 2005/0261687 A1 | 11/2005 | Garamszegi et al. |
| 2006/0173454 A1 | 8/2006 | Spitler et al. |
| 2006/0200128 A1 | 9/2006 | Mueller |
| 2006/0241600 A1 | 10/2006 | Ensign et al. |
| 2006/0264933 A1 | 11/2006 | Baker et al. |
| 2007/0043359 A1 | 2/2007 | Altarac et al. |
| 2007/0055235 A1 | 3/2007 | Janowski et al. |
| 2010/0241170 A1* | 9/2010 | Cammisa et al. ............. 606/264 |
| 2010/0331889 A1* | 12/2010 | Abdou ........................ 606/264 |

OTHER PUBLICATIONS

PCT/US08/73760 International Search Report dated Jan. 22, 2009.
Jun. 27, 2011 Office Action for Canadian Application No. 2,691,430 filed on Jun. 26, 2008.
Feb. 24, 2011 Office Action for Australian Application No. 2008270563 filed Jun. 26, 2008.
Jan. 5, 2009 International Search Report for International Application No. PCT/US2008/068393.
Jan. 5, 2009 Written Opinion of the International Searching Authority for International Application No. PCT/US2008/068393.
Oct. 26, 2012 Supplemental European Search Report for European App No. 08 77 2068, filed Jun. 26, 2008.

* cited by examiner

SPINAL STABILIZATION DEVICE

CROSS REFERENCE

This application claims benefit of priority to U.S. provisional patent application 60/946,893, filed Jun. 28, 2007, which is incorporated herein in its entirety.

BACKGROUND OF THE INVENTION

The pedicle screw, which is sometimes used as an adjunct to spinal fusion surgery, provides a means of gripping a spinal segment. The screws themselves do not fixate the spinal segment, but act as anchor points that can then be connected with a rod. The screws are usually placed at two or three consecutive spine segments and then a rod is used to connect the screws. A generally yoke-like coupler and a locking device (e.g. set screw) is typically used to compress the rod against (directly or with an intermediate element) the spinal screw head and lock the assembly. Together, the rod, coupler, and screw cooperate to stabilize and generally immobilize the spinal segments that are being fused.

Most screws and couplers are constructed such that the screw has polyaxial movement relative to the coupler prior to being locked into position. The polyaxial screw assembly allows the rod to be placed at a variety of angles relative to the angle at which the screw is placed in the pedicle. The rods and couplers of the devices often coordinate with a device (e.g., set screw) which locks the rod in place and locks the angle and position of the rod relative to the polyaxial screw.

While pedicle screw, rod, and coupler systems have many benefits, there remain challenges and inadequacies. For example, the pedicle screw, coupler, and rod systems are often made up of multiple pieces which can get dropped, fumbled during surgery, or misplaced. The multitude of pieces to a system might also mean that that several people are required to assemble and align the pieces during surgery.

Additionally, the multitude of pieces to a system can also result in a high assembled profile, which can be uncomfortable, if not painful, to a recovering patient. A high profile system can also be disruptive to the recovered patient since the systems are seldom removed once spine fusion is complete.

Furthermore, while the polyaxial nature of the system is a benefit to final alignment, one drawback to a polyaxial screw system is that before the rod is locked down, the coupler and rod can typically move freely relative to the head of the screw as other pedicle screws are implanted and as the rod is connected to another coupler. This makes the actual process of aligning and holding the coupler and rod in place prior to locking down all polyaxial screw systems more complicated—requiring more finesse and potentially multiple operators. These challenges can prolong surgery time and add cost and risk to the procedure and to patient recovery.

Thus, there is a need for pedicle screw and rod devices that are easier to distribute, store, sterilize and/or use. These and other needs are met by embodiments described herein.

SUMMARY OF THE INVENTION

The foregoing and further needs are met by embodiments set forth herein, of which at least some provide a bone attachment device comprising a bone fastener having a distal portion adapted to pierce bone and a proximal portion having a head. In some embodiments, the bone attachment device comprises a collar comprising: a collar wall defining a cavity and having at least one wall aperture; a distal portion comprising an opening and a collar seat projecting inward and supporting the head of the bone fastener; a proximal portion having a hinged lid; and a spinal rod locking device, wherein at least a portion of the spinal rod locking device is within the cavity defined by the collar wall.

In some embodiments, the bone attachment device comprises a washer. In some embodiments, the washer has a proximal end and a distal end. The washer may comprise a substantially cylindrical wall having an interior surface and an exterior surface. In some embodiments, the distal end of the washer fits over the head of the bone fastener. In some embodiments, the washer may comprise a beveled surface. In some embodiments, the beveled surface may be on the distal end of the washer. In some embodiments, the beveled surface may be on the interior surface of the cylindrical wall, in some embodiments. In some embodiments, the beveled surface may be concave, convex or planar. In some embodiments, the beveled surface is planar frustoconical. In some embodiments, the beveled surface abuts a proximal portion of the bone fastener. In some embodiments, the washer fits on the proximal portion of the bone fastener.

In some embodiments, the spinal rod locking device comprises a nut. The nut may project through an aperture of the hinged lid of the bone attachment device. In some embodiments, the nut may project through an aperture of the proximal portion of the bone attachment device. In some embodiments, the nut may fit within the cavity of the collar. In some embodiments, the nut comprises a cam surface. The cam surface may be on a distal portion of the nut. In some embodiments, the distal cam surface is adapted to impart distal force to the clamp member. In some embodiments, the nut is adapted to turn about an axis.

The nut may comprise a collar engagement member. In some embodiments, the collar engagement member is adapted to engage an inner surface of the collar. In some embodiments, the collar engagement member is adapted to engage an outer surface of the collar. In some embodiments, the collar engagement member is adapted to engage an overhang in the collar. In some embodiments, the overhang is on at least one of an inner surface of the collar and an outer surface of the collar. In some embodiments, the overhang comprises an inclined surface. In some embodiments, the collar engagement member is adapted to engage the overhang to resist proximal motion of the nut, whereby force imparted by turning of the nut about the axis is directed distally. In some embodiments, the nut is adapted to turn about an axis, and possesses a distal cam surface, which is adapted to impart distal force to a clamp member.

In some embodiments, the spinal rod locking device comprises a clamp member having a distal surface. The clamp member may comprise a cam surface. The cam surface may be on a proximal end of the clamp member. In some embodiments, the cam surface on the proximal end of the clamp member is adapted to engage or interact with the cam surface on the distal portion of the nut, whereby turning the nut imparts distal force to the clamp member. In some embodiments, at least a portion of the distal surface of the clamp member is concave, convex, or planar. In some embodiments, at least a portion of the distal surface of the clamp member is concave. In some embodiments, the surface is adapted to engage a surface of a rod extending through the wall aperture. In some embodiments, the planar, concave, or convex distal surface is adapted to engage the rod extending through the wall aperture. In some embodiments, the clamp member possesses a concave distal surface. In some embodiments, the clamp member possesses a proximal cam surface which interacts with the distal cam surface of the nut, and which is adapted to receive distal force from the nut and impart distal force to a rod extending through the wall aperture.

In some embodiments, the collar seat comprises a beveled surface. In some embodiments, the beveled surface faces the distal portion of the collar. In some embodiments, the beveled surface is planar, convex or concave frustoconical. In some embodiments, the beveled surface is on a distal portion of the collar seat. In some embodiments, the beveled surface is on a proximal portion of the collar seat.

In some embodiments, the bone attachment device comprises a collar overhang extending from a portion of the collar toward the cavity. In some embodiments, the overhang is on at least one of an inner surface of the collar and an outer surface of the collar.

The foregoing and further needs are further met by embodiments described herein, which provide a bone attachment device comprising a bone fastener having a distal portion adapted to pierce bone and a proximal portion having a head. The bone fastener further comprises a collar comprising a wall defining a cavity and having at least one wall aperture, a distal portion comprising an opening and a collar seat projecting inward and supporting the head of the bone fastener, a proximal portion having a non-cammed slot, and a spinal rod locking device, wherein at least a portion of the spinal rod locking device is within the cavity defined by the collar wall. In some embodiments, the non-cammed slot and the overhang are on an inner surface of the collar. In some embodiments, the non-cammed slot and the overhang are on an outer surface of the collar.

In some embodiments, the bone attachment device comprises a washer as described herein. The washer has a proximal end and a distal end. The washer may comprise a substantially cylindrical wall having an interior surface and an exterior surface. In some embodiments, the distal end of the washer fits over the head of the bone fastener. The washer may comprise a beveled surface. The beveled surface may be on the distal end of the washer. The beveled surface may be on the interior surface of the cylindrical wall, in some embodiments. The beveled surface may be concave, convex or planar. In some embodiments, the beveled surface is planar frustoconical. In some embodiments, the beveled surface abuts a proximal portion of the bone fastener. In some embodiments, the washer fits on the proximal portion of the bone fastener.

In some embodiments, the spinal rod locking device comprises a nut. The nut fits with the cavity of the collar. In some embodiments, the nut comprises a cam surface. The cam surface may be on a distal portion of the nut. In some embodiments, the distal cam surface is adapted to impart distal force to the clamp member. In some embodiments, the nut is adapted to turn about an axis.

The nut may comprise a collar engagement member. In some embodiments, the collar engagement member is adapted to engage an inner surface of the collar. In some embodiments, the collar engagement member is adapted to engage an outer surface of the collar. In some embodiments, the collar engagement member is adapted to engage an overhang in the collar. In some embodiments, the overhang is on at least one of an inner surface of the collar and an outer surface of the collar. In some embodiments, the overhang comprises an inclined surface. In some embodiments, the collar engagement member is adapted to engage the overhang to resist proximal motion of the nut, whereby force imparted by turning of the nut about the axis is directed distally. In some embodiments, the nut is adapted to turn about an axis, and possesses a distal cam surface, which is adapted to impart distal force to a clamp member. In some embodiments, the collar engagement member is adapted to cooperate with the non-cammed slot to engage the overhang to resist proximal motion of the nut, whereby force imparted by turning of the nut about the axis is directed distally. In some embodiments, the non-cammed slot and the overhang are on an inner surface of the collar. In some embodiments, the non-cammed slot and the overhang are on an outer surface of the collar.

In some embodiments, the spinal rod locking device comprises a clamp member having a distal surface. The clamp member may comprise a cam surface. The cam surface may be on a proximal end of the clamp member. In some embodiments, the cam surface on the proximal end of the clamp member is adapted to engage or interact with the cam surface on the distal portion of the nut, whereby turning the nut imparts distal force to the clamp member. In some embodiments, at least a portion of the distal surface of the clamp member is concave, convex, or planar. In some embodiments, at least a portion of the distal surface of the clamp member is concave. In some embodiments, the surface is adapted to engage a surface of a rod extending through the wall aperture. In some embodiments, the planar, concave, or convex distal surface is adapted to engage the rod extending through the wall aperture. In some embodiments, the clamp member possesses a concave distal surface. In some embodiments, the clamp member possesses a proximal cam surface which interacts with the distal cam surface of the nut, and which is adapted to receive distal force from the nut and impart distal force to a rod extending through the wall aperture.

In some embodiments, the collar seat comprises a beveled surface. In some embodiments, the beveled surface faces the distal portion of the collar. In some embodiments, the beveled surface is planar, convex or concave frustoconical. In some embodiments, the beveled surface is on a distal portion of the collar seat. In some embodiments, the beveled surface is on a proximal portion of the collar seat.

In some embodiments, the bone attachment device comprises a collar overhang extending from a portion of the collar toward the cavity. In some embodiments, the overhang is on at least one of an inner surface of the collar and an outer surface of the collar.

The foregoing and further needs are further met by embodiments described herein, which provide a bone attachment collar comprising a collar wall defining a cavity and having at least one wall aperture. In some embodiments, the bone attachment collar comprises a distal portion comprising an opening and a collar seat projecting inward and supporting the head of the bone fastener. In some embodiments, the bone attachment collar comprises a proximal portion having a hinged lid. Other embodiments of the bone attachment collar do not have a hinged lid. In some embodiments, the collar comprises a proximal portion having a non-cammed slot. In some embodiments, the non-cammed slot and the overhang are on an inner surface of the collar. In some embodiments, the non-cammed slot and the overhang are on an outer surface of the collar. In some embodiments, the bone attachment collar comprises a spinal rod locking device, wherein at least a portion of the spinal locking device is within the cavity defined by the collar wall.

In some embodiments, the bone attachment collar comprises a washer as described herein. The washer has a proximal end and a distal end. The washer may comprise a substantially cylindrical wall having an interior surface and an exterior surface. In some embodiments, the distal end of the washer fits over the head of the bone fastener. The washer may comprise a beveled surface. The beveled surface may be on the distal end of the washer. The beveled surface may be on the interior surface of the cylindrical wall, in some embodiments. The beveled surface may be concave, convex or planar.

In some embodiments, the beveled surface is planar frustoconical. In some embodiments, the beveled surface abuts a proximal portion of the bone fastener. In some embodiments, the washer fits on the proximal portion of the bone fastener.

In some embodiments, the bone attachment collar comprises a nut as described herein. The nut may project through an aperture of the hinged lid of the bone attachment collar. In some embodiments, the nut fits with the cavity of the collar. In some embodiments, the nut may project through an aperture of the proximal portion of the bone attachment collar. In some embodiments, the nut comprises a cam surface. The cam surface may be on a distal portion of the nut. In some embodiments, the distal cam surface is adapted to impart distal force to the clamp member. In some embodiments, the nut is adapted to turn about an axis.

In some embodiments, the nut may comprise a collar engagement member. In some embodiments, the collar engagement member is adapted to engage an inner surface of the collar. In some embodiments, the collar engagement member is adapted to engage an outer surface of the collar. In some embodiments, the collar engagement member is adapted to engage an overhang in the collar. In some embodiments, the overhang is on at least one of an inner surface of the collar and an outer surface of the collar. In some embodiments, the overhang comprises an inclined surface. In some embodiments, the collar engagement member is adapted to engage the overhang to resist proximal motion of the nut, whereby force imparted by turning of the nut about the axis is directed distally. In some embodiments, the nut is adapted to turn about an axis, and possesses a distal cam surface, which is adapted to impart distal force to a clamp member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on an inner surface of the collar. In some embodiments, the non-cammed slot and the overhang are on an outer surface of the collar.

In some embodiments, the spinal rod locking device comprises a clamp member having a distal surface. The clamp member may comprise a cam surface. The cam surface may be on a proximal end of the clamp member. In some embodiments, the cam surface on the proximal end of the clamp member is adapted to engage or interact with the cam surface on the distal portion of the nut, whereby turning the nut imparts distal force to the clamp member. In some embodiments, at least a portion of the distal surface of the clamp member is concave, convex, or planar. In some embodiments, at least a portion of the distal surface of the clamp member is concave. In some embodiments, the surface is adapted to engage a surface of a rod extending through the wall aperture. In some embodiments, the planar, concave, or convex distal surface is adapted to engage the rod extending through the wall aperture. In some embodiments, the clamp member possesses a concave distal surface. In some embodiments, the clamp member possesses a proximal cam surface which interacts with the distal cam surface of the nut, and which is adapted to receive distal force from the nut and impart distal force to a rod extending through the wall aperture.

In some embodiments, the collar seat comprises a beveled surface. In some embodiments, the beveled surface faces the distal portion of the collar. In some embodiments, the beveled surface is planar, convex or concave frustoconical. In some embodiments, the beveled surface is on a distal portion of the collar seat. In some embodiments, the beveled surface is on a proximal portion of the collar seat.

In some embodiments, the bone attachment collar comprises a collar overhang extending from a portion of the collar toward the cavity. In some embodiments, the overhang is on at least one of an inner surface of the collar and an outer surface of the collar.

Provided herein is a spinal stabilizer comprising at least two bone attachment devices as described herein and a bone stabilization rod extending through the wall apertures of at least two bone attachment devices. The bone attachment devices are adapted to lock the rod in place, thereby preventing translational motion of the rod. In some embodiments, spinal rod locking devices of the bone attachment devices are adapted to lock the rod in place, thereby preventing translational motion of the rod. In some embodiments, spinal rod locking devices of the bone attachment devices are adapted to lock the orientation of the bone fastener relative to the rod when the rod is locked in place.

In some embodiments of the spinal stabilizer, at least one of, or both of the two bone attachment devices comprise a bone fastener having a distal portion adapted to pierce bone and a proximal portion having a head. At least one of, or both of, the two bone attachment devices may comprise a collar comprising a collar wall defining a cavity and having at least one wall aperture. The collar may comprise a distal portion comprising an opening and a collar seat projecting inward and supporting the head of the bone fastener. In some embodiments of the spinal stabilizer, the proximal portion of at least one of the two bone attachment devices may have a hinged lid and a spinal rod locking device, wherein at least a portion of the spinal rod locking device is within the cavity defined by the collar wall. In some embodiments, the collar comprises a proximal portion having a non-cammed slot and a spinal rod locking device, wherein at least a portion of the spinal rod locking device is within the cavity defined by the collar wall. In some embodiments of the spinal stabilizer, at least one of, or both of the two bone attachment devices comprises an opening and a collar seat projecting inward and supporting the head of the bone fastener, and a spinal rod locking device.

In some embodiments, the rod has a substantially uniform cross section. In some embodiments, the cross section is at least one of circular, elliptical, and polygonal. In some embodiments, the polygonal cross section is at least one of triangular, quadrangular (e.g. square, rectangular, rhomboidal, trapezoidal), pentagonal, hexagonal, heptagonal, and octagonal.

In some embodiments, at least one bone attachment device of the spinal stabilizer comprises a washer as described herein. The washer has a proximal end and a distal end. The washer may comprise a substantially cylindrical wall having an interior surface and an exterior surface. In some embodiments, the distal end of the washer fits over the head of the bone fastener. The washer may comprise a beveled surface. The beveled surface may be on the distal end of the washer. The beveled surface may be on the interior surface of the cylindrical wall, in some embodiments. The beveled surface may be concave, convex or planar. In some embodiments, the beveled surface is planar frustoconical. In some embodiments, the beveled surface abuts a proximal portion of the bone fastener. In some embodiments, the washer fits on the proximal portion of the bone fastener.

In some embodiments, the at least one spinal rod locking device bone attachment device of the spinal stabilizer comprises a nut as described herein. In some embodiments, the nut may project through an aperture of the hinged lid of the bone attachment device. In some embodiments, the nut fits with the cavity of the collar. In some embodiments, the nut may project through an aperture of the proximal portion of the bone attachment collar. In some embodiments, the nut comprises a cam surface. The cam surface may be on a distal portion of the nut. In some embodiments, the distal cam surface is adapted to impart distal force to the clamp member. In some embodiments, the nut is adapted to turn about an axis.

In some embodiments, the at least one spinal rod locking device bone attachment device of the spinal stabilizer comprises a nut comprising a collar engagement member. In some embodiments, the collar engagement member is adapted to engage an overhang in the collar. In some embodiments, the overhang is on at least one of an inner surface of the collar and an outer surface of the collar. In some embodiments, the overhang comprises an inclined surface. In some embodiments, the collar engagement member is adapted to engage the overhang to resist proximal motion of the nut, whereby force imparted by turning of the nut about the axis is directed distally. In some embodiments, the nut is adapted to turn about an axis, and possesses a distal cam surface, which is adapted to impart distal force to a clamp member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on an inner surface of the collar. In some embodiments, the non-cammed slot and the overhang are on an outer surface of the collar.

In some embodiments, the spinal rod locking device of at least one spinal stabilizer comprises a clamp member having a distal surface. The clamp member may comprise a cam surface. The cam surface may be on a proximal end of the clamp member. In some embodiments, the cam surface on the proximal end of the clamp member is adapted to engage or interact with the cam surface on the distal portion of the nut, whereby turning the nut imparts distal force to the clamp member. In some embodiments, at least a portion of the distal surface of the clamp member is concave, convex, or planar. In some embodiments, at least a portion of the distal surface of the clamp member is concave. In some embodiments, the surface is adapted to engage a surface of a rod extending through the wall aperture. In some embodiments, the planar, concave, or convex distal surface is adapted to engage the rod extending through the wall aperture. In some embodiments, the clamp member possesses a concave distal surface. In some embodiments, the clamp member possesses a proximal cam surface which interacts with the distal cam surface of the nut, and which is adapted to receive distal force from the nut and impart distal force to a rod extending through the wall aperture.

In some embodiments, the collar seat of at least one bone attachment device of the spinal stabilizer comprises a beveled surface. In some embodiments, the beveled surface faces the distal portion of the collar. In some embodiments, the beveled surface is planar, convex or concave frustoconical. In some embodiments, the beveled surface is on a distal portion of the collar seat. In some embodiments, the beveled surface is on a proximal portion of the collar seat.

In some embodiments, at least one bone attachment device of the spinal stabilizer comprises a collar overhang extending from a portion of the collar toward the cavity. In some embodiments, the overhang is on at least one of an inner surface of the collar and an outer surface of the collar.

Provided herein is a method for implanting a spinal stabilization device comprising delivering a first bone attachment device to a first pedicle, wherein the first bone attachment device comprises a first bone fastener having a distal portion adapted to pierce bone and a proximal portion having a head, and a first collar comprising a collar wall defining a cavity and having at least one wall aperture, a distal portion comprising an opening and a collar seat projecting inward and supporting a head of the bone fastener, a proximal portion having a hinged lid, and a spinal rod locking device, wherein at least a portion of the spinal rod locking device is within the cavity defined by the collar wall. The method may further comprise fastening the distal portion of the first bone fastener to the first pedicle. In some embodiments, the method comprises delivering a second bone attachment device to a second pedicle, wherein the second bone attachment device comprises a second bone fastener having a distal portion adapted to pierce bone and a proximal portion having a head, and a second collar comprising: a collar wall defining a cavity and having at least one wall aperture; a distal portion comprising an opening and a collar seat projecting inward and supporting a head of the bone fastener; and a spinal rod locking device, wherein at least a portion of the spinal rod locking device is within the cavity defined by the collar wall. In some embodiments, the method comprises placing a rod within the aperture of the first bone attachment device. The method may further comprise placing the rod within the aperture of the second bone attachment device. In some embodiments, the method further comprises locking the first bone attachment device, wherein the locking comprises pivoting the hinged lid toward the first collar over the rod, and engaging an overhang of the first collar with a collar engagement member of the spinal rod locking device of the first collar. The method may further comprise locking the second bone attachment device. The locking steps may lock the rod in place, thereby preventing translational motion of the rod.

In some embodiments, the second collar of the second bone attachment device comprises a proximal portion having a hinged lid. In some embodiments of the method, locking the second bone attachment device comprises: pivoting the hinged lid toward the first collar over the rod; and engaging an overhang of the first collar with a collar engagement member of the spinal rod locking device of the first collar.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
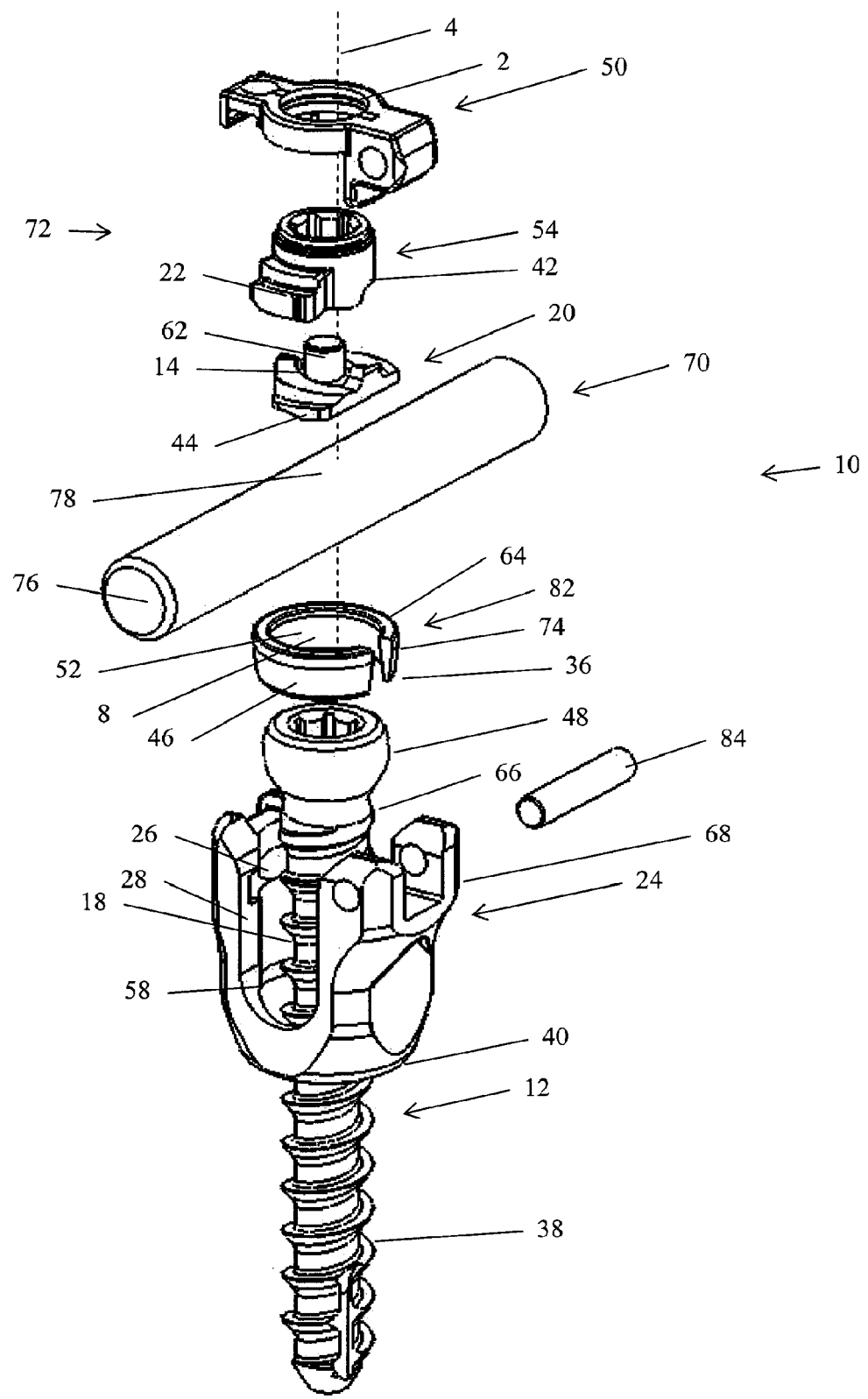
FIG. 1A shows an exploded view of an embodiment of a hinged bone attachment device including a rod.

There are described herein bone attachment devices (pedicle screws) and spinal stabilization devices employing such pedicle screws. Pedicle screws described herein provide certain advantages. In some embodiments, such advantages include low profile. In some embodiments, such advantages include the convenience of providing a collar with a hinged cap, whereby the collar and the cap will not easily become separated prior to or during a surgical procedure. Other advantages and characteristics of the pedicle screws will be apparent upon consideration of the description herein and the drawings appended hereto.

Some embodiments described herein provide a bone attachment device, comprising: (a) a bone fastener having a distal portion adapted to pierce bone and a proximal portion having a head; (b) a collar comprising: (i) a collar wall defining a cavity and having at least one wall aperture; (ii) a distal portion comprising an opening and a collar seat projecting inward and supporting the head of the bone fastener; (iii) a proximal portion having a hinged lid; and (iv) a spinal rod locking device, wherein at least a portion of the spinal rod locking device is within the cavity defined by the collar wall. In some embodiments, the method further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises a beveled surface. In some embodiments, the beveled surface is on the interior surface of the cylindrical wall. In some embodiments, the beveled surface is concave, convex or planar.

Some embodiments described herein provide a bone attachment device, comprising: (a) a bone fastener having a distal portion adapted to pierce bone and a proximal portion having a head; (b) a collar comprising: (i) a collar wall defining a cavity and having at least one wall aperture; (ii) a distal portion comprising an opening and a collar seat projecting inward and supporting the head of the bone fastener; (iii) a proximal portion having a hinged lid; and (iv) a spinal rod locking device, wherein at least a portion of the spinal rod locking device is within the cavity defined by the collar wall, further wherein the spinal rod locking device comprises a nut. In some embodiments, the hinged lid has a lid aperture through which the nut projects. In some embodiments, the nut comprises a cam surface. In some embodiments, the cam surface is on a distal portion of the nut. In some embodiments, the nut further comprises a collar engagement member. In some embodiments, the collar engagement member is adapted to engage at least one of an inner surface of the collar and an outer surface of the collar. In some embodiments, the spinal rod locking device comprises a clamp member having a distal surface. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of a rod extending through the wall aperture.

Some embodiments described herein provide a bone attachment device, comprising: (a) a bone fastener having a distal portion adapted to pierce bone and a proximal portion having a head; (b) a collar comprising: (i) a collar wall defining a cavity and having at least one wall aperture; (ii) a distal portion comprising an opening and a collar seat projecting inward and supporting the head of the bone fastener; (iii) a proximal portion having a hinged lid; and (iv) a spinal rod locking device, wherein at least a portion of the spinal rod locking device is within the cavity defined by the collar wall, further wherein the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a bone attachment device, comprising: (a) a bone fastener having a distal portion adapted to pierce bone and a proximal portion having a head; (b) a collar comprising: (i) a collar wall defining a cavity and having at least one wall aperture; (ii) a distal portion comprising an opening and a collar seat projecting inward and supporting the head of the bone fastener; (iii) a proximal portion having a hinged lid; and (iv) a spinal rod locking device, wherein at least a portion of the spinal rod locking device is within the cavity defined by the collar wall, wherein the spinal rod locking device comprises (a) a nut; and (b) a clamp member. In some embodiments, the bone attachment device further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises a beveled surface. In some embodiments, the beveled surface is on the interior surface of the cylindrical wall. In some embodiments, the beveled surface is concave, convex or planar. In some embodiments, the hinged lid has a lid aperture through which the nut projects. In some embodiments, the nut comprises a cam surface. In some embodiments, the cam surface is on a distal portion of the nut. In some embodiments, the nut further comprises a collar engagement member. In some embodiments, the collar engagement member is adapted to engage at least one of an inner surface of the collar and an outer surface of the collar. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of a rod extending through the wall aperture. In some embodiments, the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a bone attachment device, comprising: (a) a bone fastener having a distal portion adapted to pierce bone and a proximal portion having a head; (b) a collar comprising: (i) a collar wall defining a cavity and having at least one wall aperture; (ii) a distal portion comprising an opening and a collar seat projecting inward and supporting the head of the bone fastener; (iii) a proximal portion having a hinged lid; and (iv) a spinal rod locking device, wherein at least a portion of the spinal rod locking device is within the cavity defined by the collar wall, wherein the bone attachment device further comprises a washer fitting on the proximal portion of the bone fastener, wherein the spinal rod locking device comprises: (a) a nut, which is adapted to turn about an axis, and which possesses a distal cam surface, which is adapted to impart distal force to a clamp member; and (b) the clamp member possessing a proximal cam surface, which interacts with the distal cam surface of the nut, and which is adapted to receive distal force from the nut and impart distal force to a rod extending through the wall aperture. In some embodiments, the washer possesses a beveled surface. In some embodiments, the beveled surface is on a distal end of the washer. In some embodiments, the beveled surface is convex, concave or planar frustoconical. In some embodiments, the beveled surface is planar frustoconical. In some embodiments, the nut comprises a collar engagement member.

Some embodiments described herein provide a bone attachment device, comprising: (a) a bone fastener having a distal portion adapted to pierce bone and a proximal portion having a head; (b) a collar comprising: (i) a collar wall defining a cavity and having at least one wall aperture; (ii) a distal portion comprising an opening and a collar seat projecting inward and supporting the head of the bone fastener; (iii) a proximal portion having a hinged lid; and (iv) a spinal rod locking device, wherein at least a portion of the spinal rod locking device is within the cavity defined by the collar wall, wherein the spinal rod locking device comprises a nut, which is adapted to turn about an axis, wherein the nut comprises a collar engagement member and wherein the collar engagement member is adapted to engage an overhang in the collar. In some embodiments, the overhang comprises an inclined surface. In some embodiments, the collar engagement member is adapted to engage the overhang to resist proximal motion of the nut, whereby force imparted by turning of the nut about the axis is directed distally. In some embodiments, the overhang is on at least one of an inner surface of the collar and an outer surface of the collar. In some embodiments, the clamp member possesses a planar, concave or convex distal surface adapted to engage a rod extending through the wall aperture. In some embodiments, the clamp member possesses a concave distal surface.

Some embodiments described herein provide a bone attachment device, comprising: (a) a bone fastener having a distal portion adapted to pierce bone and a proximal portion having a head; (b) a collar comprising: (i) a collar wall defining a cavity and having at least one wall aperture; (ii) a distal portion comprising an opening and a collar seat projecting inward and supporting the head of the bone fastener; (iii) a proximal portion having a hinged lid; and (iv) a spinal rod locking device, wherein at least a portion of the spinal rod locking device is within the cavity defined by the collar wall, wherein the bone attachment device further comprises: (a) a collar overhang extending from a proximal portion of the collar toward the cavity; and (b) a washer having a beveled surface at a distal end, wherein the beveled surface abuts a proximal portion of the bone fastener, wherein the spinal rod locking device comprises (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally, and (d) a clamp member possessing a proximal cam surface, which interacts with the distal cam surface of the nut, and which is adapted to receive distal force from the nut and impart distal force to a rod extending through the wall aperture, and further possessing a distal surface, at least a portion of which is planar, convex or concave, and is adapted to engage the rod extending through the wall aperture. In some embodiments, the overhang comprises an inclined surface. In some embodiments, the overhang is on at least one of an inner surface of the collar and an outer surface of the collar. In some embodiments, the beveled surface is planar frustoconical. In some embodiments, the distal surface of the clamp member is concave.

Some embodiments described herein provide a bone attachment device, comprising: (a) a bone fastener having a distal portion adapted to pierce bone and a proximal portion having a head; (b) a collar comprising: (i) a collar wall defining a cavity and having at least one wall aperture; (ii) a distal portion comprising an opening and a collar seat projecting inward and supporting the head of the bone fastener; (iii) a proximal portion having a hinged lid; and (iv) a spinal rod locking device, wherein at least a portion of the spinal rod locking device is within the cavity defined by the collar wall, wherein the bone attachment device of further comprises: (a) a collar overhang extending from a proximal portion of the collar toward the cavity; and (b) a washer having a beveled surface at a distal end, wherein the beveled surface abuts a proximal portion of the bone fastener, wherein the beveled surface is planar frustoconical, and wherein the spinal rod locking device comprises: (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (d) a clamp member possessing a proximal cam surface, which interacts with the distal cam surface of the nut, and which is adapted to receive distal force from the nut and impart distal force to a rod extending through the wall aperture, and further possessing a distal surface, at least a portion of which is concave, and is adapted to engage the rod extending through the wall aperture. In some embodiments, the overhang comprises an inclined surface. In some embodiments, the overhang is on at least one of an inner surface of the collar and an outer surface of the collar. In some embodiments, the collar seat has a beveled surface, which is planar, convex or concave frustoconical. In some embodiments, the beveled surface is on at least one of a distal and a proximal portion of the collar seat.

Some embodiments described herein provide a spinal stabilizer, comprising: (a) at least two bone attachment devices, comprising: (i) a bone fastener having a distal portion adapted to pierce bone and a proximal portion having a head; and (ii) a collar comprising: (A) a collar wall defining a cavity and having at least one wall aperture, (B) a distal portion comprising an opening and a collar seat projecting inward and supporting the head of the bone fastener, (C) a proximal portion having a hinged lid, and (D) a spinal rod locking device, wherein at least a portion of the spinal rod locking device is within the cavity defined by the collar wall; and (b) a bone stabilization rod extending through the wall apertures of at least two bone attachment devices; wherein the spinal rod locking devices are adapted to lock the rod in place, thereby preventing translational motion of the rod. In some embodiments, the rod has a substantially uniform cross section. In some embodiments, the cross section is circular, elliptical, or polygonal. In some embodiments, the cross section is circular. In some embodiments, the cross section is polygonal. In some embodiments, the polygonal cross section is triangular, quadrangular (e.g. square, rectangular, rhomboidal, trapezoidal), pentagonal, hexagonal, heptagonal or octagonal. In some embodiments, the bone attachment device further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises a beveled surface. In some embodiments, the beveled surface is on the interior surface of the cylindrical wall. In some embodiments, the beveled surface is concave, convex or planar frustoconical. In some embodiments, the spinal rod locking device comprises a nut. In some embodiments, the hinged lid has a lid aperture through which the nut projects. In some embodiments, the nut comprises a cam surface. In some embodiments, the cam surface is on a distal portion of the nut. In some embodiments, the nut further comprises a collar engagement member. In some embodiments, the collar engagement member is adapted to engage at least one of an inner surface of the collar and an outer surface of the collar. In some embodiments, the spinal rod locking device comprises a clamp member having a distal surface. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of the rod. In some embodiments, the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a spinal stabilizer, comprising: (a) at least two bone attachment devices, comprising: (i) a bone fastener having a distal portion adapted to pierce bone and a proximal portion having a head; and (ii) a collar comprising: (A) a collar wall defining a cavity and having at least one wall aperture, (B) a distal portion comprising an opening and a collar seat projecting inward and supporting the head of the bone fastener, (C) a proximal portion having a hinged lid, and (D) a spinal rod locking device, wherein at least a portion of the spinal rod locking device is within the cavity defined by the collar wall; and (b) a bone stabilization rod extending through the wall apertures of at least two bone attachment devices; wherein the spinal rod locking devices are adapted to lock the rod in place, thereby preventing translational motion of the rod, wherein the spinal rod locking device comprises: (a) a nut; and (b) a clamp member. In some embodiments, the spinal stabilizer further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises a beveled surface. In some embodiments, the beveled surface is on the interior surface of the cylindrical wall. In some embodiments, the beveled surface is concave, convex or planar. In some embodiments, the hinged lid has a lid aperture through which the nut projects. In some embodiments, the nut comprises a cam surface. In some embodiments, the cam surface is on a distal portion of the nut. In some embodiments, the nut further comprises a collar engagement member. In some embodiments, the collar engagement member is adapted to engage at least one of an inner surface of the collar and an outer surface of the collar. In some embodiments, the spinal rod locking device comprises a clamp member having a distal surface. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of the rod. In some embodiments, the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a spinal stabilizer, comprising: (a) at least two bone attachment devices, comprising: (i) a bone fastener having a distal portion adapted to pierce bone and a proximal portion having a head; and (ii) a collar comprising: (A) a collar wall defining a cavity and having at least one wall aperture, (B) a distal portion comprising an opening and a collar seat projecting inward and supporting the head of the bone fastener, (C) a proximal portion having a hinged lid, and (D) a spinal rod locking device, wherein at least a portion of the spinal rod locking device is within the cavity defined by the collar wall; and (b) a bone stabilization rod extending through the wall apertures of at least two bone attachment devices; wherein the spinal rod locking devices are adapted to lock the rod in place, thereby preventing translational motion of the rod, wherein the spinal stabilizer further comprises a washer fitting on the proximal portion of the bone fastener, wherein the spinal rod locking device comprises a nut, which is adapted to turn about an axis, and which possesses a distal cam surface, which is adapted to impart distal force to a clamp member; and the clamp member, possesses a proximal cam surface, which interacts with the distal cam surface of the nut, and which is adapted to receive distal force from the nut and impart distal force to the rod extending through the wall aperture. In some embodiments, the washer possesses a beveled surface. In some embodiments, the beveled surface is on a distal end of the washer. In some embodiments, the beveled surface is convex, concave or planar frustoconical. In some embodiments, the beveled surface is planar frustoconical. In some embodiments, the nut comprises a collar engagement member. In some embodiments, the spinal rod locking device comprises a nut, which is adapted to turn about an axis, wherein the nut comprises a collar engagement member and wherein the collar engagement member is adapted to engage an overhang in the collar. In some embodiments, the overhang is on at least one of an inner surface of the collar and an outer surface of the collar. In some embodiments, the overhang comprises an inclined surface. In some embodiments, the collar engagement member is adapted to engage the overhang to resist proximal motion of the nut, whereby force imparted by turning of the nut about the axis is directed distally. In some embodiments, the clamp member possesses a planar, concave or convex distal surface adapted to engage a rod extending through the wall aperture. In some embodiments, the clamp member possesses a concave distal surface.

Some embodiments described herein provide a spinal stabilizer, comprising: (a) at least two bone attachment devices, comprising: (i) a bone fastener having a distal portion adapted to pierce bone and a proximal portion having a head; and (ii) a collar comprising: (A) a collar wall defining a cavity and having at least one wall aperture, (B) a distal portion comprising an opening and a collar seat projecting inward and supporting the head of the bone fastener, (C) a proximal portion having a hinged lid, and (D) a spinal rod locking device, wherein at least a portion of the spinal rod locking device is within the cavity defined by the collar wall; and (b) a bone stabilization rod extending through the wall apertures of at least two bone attachment devices; wherein the spinal rod locking devices are adapted to lock the rod in place, thereby preventing translational motion of the rod, wherein the spinal stabilization device further comprises: (a) a collar overhang extending from a proximal portion of the collar toward the cavity; (b) a washer having a beveled surface at a distal end, wherein the beveled surface abuts a proximal portion of the bone fastener, wherein the spinal rod locking device comprises (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (d) a clamp member possessing a proximal cam surface, which interacts with the distal cam surface of the nut, and which is adapted to receive distal force from the nut and impart distal force to a rod extending through the wall aperture, and further possessing a distal surface, at least a portion of which is planar, convex or concave, and is adapted to engage the rod extending through the wall aperture. In some embodiments, the overhang is on at least one of an inner surface of the collar and an outer surface of the collar. In some embodiments, the overhang comprises an inclined surface. In some embodiments, the beveled surface is planar frustoconical. In some embodiments, the distal surface of the clamp member is concave.

Some embodiments described herein provide a spinal stabilizer, comprising: (a) at least two bone attachment devices, comprising: (i) a bone fastener having a distal portion adapted to pierce bone and a proximal portion having a head; and (ii) a collar comprising: (A) a collar wall defining a cavity and having at least one wall aperture, (B) a distal portion comprising an opening and a collar seat projecting inward and supporting the head of the bone fastener, (C) a proximal portion having a hinged lid, and (D) a spinal rod locking device, wherein at least a portion of the spinal rod locking device is within the cavity defined by the collar wall; and (b) a bone stabilization rod extending through the wall apertures of at least two bone attachment devices; wherein the spinal rod locking devices are adapted to lock the rod in place, thereby preventing translational motion of the rod, wherein the spinal stabilizer further comprises (a) a collar overhang extending from a proximal portion of the collar toward the cavity; (b) a washer having a beveled surface at a distal end, wherein the beveled surface abuts a proximal portion of the bone fastener, wherein the beveled surface is planar frustoconical, wherein the spinal rod locking device comprises: (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (d) a clamp member possessing a proximal cam surface, which interacts with the distal cam surface of the nut, and which is adapted to receive distal force from the nut and impart distal force to a rod extending through the wall aperture, and further possessing a distal surface, at least a portion of which is concave, and is adapted to engage the rod extending between the wall aperture. In some embodiments, the overhang is on at least one of an inner surface of the collar and an outer surface of the collar. In some embodiments, the overhang comprises an inclined surface. In some embodiments, the collar seat has a beveled surface, which is planar, convex or concave frustoconical. In some embodiments, the beveled surface is on at least one of a distal portion and a proximal portion of the collar seat. In some embodiments, the spinal rod locking devices are adapted to lock the orientation of the bone fastener relative to the rod when the rod is locked in place.

Some embodiments described herein provide a bone attachment collar, comprising: (a) a collar wall defining a cavity and having at least one wall aperture; (b) a distal portion comprising an opening and a collar seat projecting inward and supporting a head of a bone fastener; (c) a proximal portion having a hinged lid; and (d) a spinal rod locking device, wherein at least a portion of the spinal locking device is within the cavity defined by the collar wall, wherein the bone attachment collar further comprises a washer. In some embodiments, the washer comprises a substantially cylindrical wall having an interior surface and an exterior surface; and the washer has a proximal end and a distal end. In some embodiments, the distal end of the washer is adapted to fit over a proximal portion of a bone fastener. In some embodiments, the distal end of the washer comprises a beveled surface. In some embodiments, the beveled surface is on the interior surface of the cylindrical wall. In some embodiments, the beveled surface is concave, convex or planar. In some embodiments, the spinal rod locking device comprises a nut. In some embodiments, the hinged lid has a lid aperture through which the nut projects. In some embodiments, the nut comprises a cam surface. In some embodiments, the cam surface is on a distal portion of the nut. In some embodiments, the nut further comprises a collar engagement member. In some embodiments, the collar engagement member is adapted to engage at least one of an inner surface of the collar and an outer surface of the collar. In some embodiments, the spinal rod locking device comprises a clamp member having a distal surface. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of a rod extending through the wall aperture. In some embodiments, the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a bone attachment collar, comprising: (a) a collar wall defining a cavity and having at least one wall aperture; (b) a distal portion comprising an opening and a collar seat projecting inward and supporting a head of a bone fastener; (c) a proximal portion having a hinged lid; and (d) a spinal rod locking device, wherein at least a portion of the spinal locking device is within the cavity defined by the collar wall. In some embodiments, the spinal rod locking device comprises: (a) a nut; and (b) a clamp member. In some embodiments, the bone attachment collar, further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises a beveled surface. In some embodiments, the beveled surface is on the interior surface of the cylindrical wall. In some embodiments, the beveled surface is concave, convex or planar. In some embodiments, the hinged lid has a lid aperture through which the nut projects. In some embodiments, the nut comprises a cam surface. In some embodiments, the cam surface is on a distal portion of the nut. In some embodiments, the nut further comprises a collar engagement member. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of a rod extending through the wall aperture. In some embodiments, the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a bone attachment collar, comprising: (a) a collar wall defining a cavity and having at least one wall aperture; (b) a distal portion comprising an opening and a collar seat projecting inward and supporting a head of a bone fastener; (c) a proximal portion having a hinged lid; and (d) a spinal rod locking device, wherein at least a portion of the spinal locking device is within the cavity defined by the collar wall, wherein the bone attachment collar further comprises a washer fitting on the proximal portion of the bone fastener, wherein the spinal rod locking device comprises: (a) a nut, which is adapted to turn about an axis, and which possesses a distal cam surface, which is adapted to impart distal force to a clamp member; and the clamp member, possesses a proximal cam surface, which interacts with the distal cam surface of the nut, and which is adapted to receive distal force from the nut and impart distal force to a rod extending through the wall aperture. In some embodiments, the washer possesses a beveled surface. In some embodiments, the beveled surface is on a distal end of the washer. In some embodiments, the beveled surface is convex, concave or planar frustoconical. In some embodiments, the beveled surface is planar frustoconical. In some embodiments, the nut comprises a collar engagement member. In some embodiments, the spinal rod locking device comprises a nut, which is adapted to turn about an axis, wherein the nut comprises a collar engagement member and wherein the collar engagement member is adapted to engage an overhang in the collar. In some embodiments, the overhang is on at least one of an inner surface of the collar and an outer surface of the collar. In some embodiments, the overhang comprises an inclined surface. In some embodiments, the collar engagement member is adapted to engage the overhang to resist proximal motion of the nut, whereby force imparted by turning of the nut about the axis is directed distally. In some embodiments, the clamp member possesses a planar, concave or convex distal surface adapted to engage a rod extending through the wall aperture. In some embodiments, the clamp member possesses a concave distal surface.

Some embodiments described herein provide a bone attachment collar, comprising: (a) a collar wall defining a cavity and having at least one wall aperture; (b) a distal portion comprising an opening and a collar seat projecting inward and supporting a head of a bone fastener; (c) a proximal portion having a hinged lid; and (d) a spinal rod locking device, wherein at least a portion of the spinal locking device is within the cavity defined by the collar wall, wherein the bone attachment collar further comprises: (a) a collar overhang extending from a proximal portion of the collar toward the cavity; and (b) a washer having a beveled surface at a distal end, wherein the beveled surface abuts a proximal portion of the bone fastener, wherein the spinal rod locking device comprises: (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (d) a clamp member possessing a proximal cam surface, which interacts with the distal cam surface of the nut, and which is adapted to receive distal force from the nut and impart distal force to a rod extending through the wall aperture, and further possessing a distal surface, at least a portion of which is planar, convex or concave, and is adapted to engage the rod extending through the wall aperture. In some embodiments, the overhang is on at least one of an inner surface of the collar and an outer surface of the collar. In some embodiments, the overhang comprises an inclined surface. In some embodiments, the beveled surface is planar frustoconical. In some embodiments, the distal surface of the clamp member is concave.

Some embodiments described herein provide a bone attachment collar, comprising: (a) a collar wall defining a cavity and having at least one wall aperture; (b) a distal portion comprising an opening and a collar seat projecting inward and supporting a head of a bone fastener; (c) a proximal portion having a hinged lid; and (d) a spinal rod locking device, wherein at least a portion of the spinal locking device is within the cavity defined by the collar wall, wherein the bone attachment collar further comprises: (a) a collar overhang extending from a proximal portion of the collar toward the cavity; and (b) a washer having a beveled surface at a distal end, wherein the beveled surface abuts a proximal portion of the bone fastener, wherein the beveled surface is planar frustoconical; wherein the spinal rod locking device comprises: a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and a clamp member possessing a proximal cam surface, which interacts with the distal cam surface of the nut, and which is adapted to receive distal force from the nut and impart distal force to a rod extending through the wall aperture, and further possessing a distal surface, at least a portion of which is concave, and is adapted to engage the rod extending through the wall aperture. In some embodiments, the overhang is on at least one of an inner surface of the collar and an outer surface of the collar. In some embodiments, the overhang comprises an inclined surface. In some embodiments, the collar seat has a beveled surface, which is planar, convex or concave frustoconical. In some embodiments, the beveled surface is on at least one of a distal portion and a proximal portion of the collar seat.

Some embodiments described herein provide a bone attachment device, comprising: (a) a bone fastener having a distal portion adapted to pierce bone and a proximal portion having a head; and (b) a collar comprising: (i) a collar wall defining a cavity and having at least one wall aperture, (ii) a distal portion comprising an opening and a collar seat projecting inward and supporting the head of the bone fastener, (iii) a proximal portion having a non-cammed slot, and (iv) a spinal rod locking device, wherein at least a portion of the spinal rod locking device is within the cavity defined by the collar wall. In some embodiments, the bone attachment device further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises a beveled surface. In some embodiments, the beveled surface is on the interior surface of the cylindrical wall. In some embodiments, the beveled surface is concave, convex or planar. In some embodiments, the spinal rod locking device comprises a nut. In some embodiments, the nut fits with the cavity. In some embodiments, the nut comprises a cam surface. In some embodiments, the cam surface is on a distal portion of the nut. In some embodiments, the nut further comprises a collar engagement member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the spinal rod locking device comprises a clamp member having a distal surface. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of a rod extending through the wall aperture. In some embodiments, the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a bone attachment device, comprising: (a) a bone fastener having a distal portion adapted to pierce bone and a proximal portion having a head; and (b) a collar comprising: (i) a collar wall defining a cavity and having at least one wall aperture, (ii) a distal portion comprising an opening and a collar seat projecting inward and supporting the head of the bone fastener, (iii) a proximal portion having a non-cammed slot, and (iv) a spinal rod locking device, wherein at least a portion of the spinal rod locking device is within the cavity defined by the collar wall, wherein the spinal rod locking device comprises: (a) a nut; and (b) a clamp member. In some embodiments, the bone attachment device further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises a beveled surface.

Some embodiments described herein provide a bone attachment device, comprising: (a) a bone fastener having a distal portion adapted to pierce bone and a proximal portion having a head; and (b) a collar comprising: (i) a collar wall defining a cavity and having at least one wall aperture, (ii) a distal portion comprising an opening and a collar seat projecting inward and supporting the head of the bone fastener, (iii) a proximal portion having a non-cammed slot, and (iv) a spinal rod locking device, wherein at least a portion of the spinal rod locking device is within the cavity defined by the collar wall, wherein the beveled surface is on the interior surface of the cylindrical wall. In some embodiments, the beveled surface is concave, convex or planar. In some embodiments, the proximal portion of the collar comprises an aperture through which the nut projects. In some embodiments, the nut comprises a cam surface. In some embodiments, the cam surface is on a distal portion of the nut. In some embodiments, the nut further comprises a collar engagement member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of a rod extending through the wall aperture. In some embodiments, the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a bone attachment device, comprising: (a) a bone fastener having a distal portion adapted to pierce bone and a proximal portion having a head; and (b) a collar comprising: (i) a collar wall defining a cavity and having at least one wall aperture, (ii) a distal portion comprising an opening and a collar seat projecting inward and supporting the head of the bone fastener, (iii) a proximal portion having a non-cammed slot, and (iv) a spinal rod locking device, wherein at least a portion of the spinal rod locking device is within the cavity defined by the collar wall, wherein the bone attachment device further comprises a washer fitting on the proximal portion of the bone fastener, wherein the spinal rod locking device comprises: (a) a nut, which is adapted to turn about an axis, and which possesses a distal cam surface, which is adapted to impart distal force to a clamp member; and (b) the clamp member possessing a proximal cam surface, which interacts with the distal cam surface of the nut, and which is adapted to receive distal force from the nut and impart distal force to a rod extending through the wall aperture. In some embodiments, the washer possesses a beveled surface. In some embodiments, the beveled surface is on a distal end of the washer. In some embodiments, the beveled surface is convex, concave or planar frustoconical. In some embodiments, the beveled surface is planar frustoconical. In some embodiments, the nut comprises a collar engagement member. In some embodiments, the collar engagement member is adapted to engage an overhang in the collar. In some embodiments, the overhang is on at least one of an inner surface of the collar and an outer surface of the collar. In some embodiments, the collar engagement member is adapted to engage the overhang to resist proximal motion of the nut, whereby force imparted by turning of the nut about the axis is directed distally. In some embodiments, the clamp member possesses a planar, concave or convex distal surface adapted to engage a rod extending through the wall aperture. In some embodiments, the clamp member possesses a concave distal surface.

Some embodiments described herein provide a bone attachment device, comprising: (a) a bone fastener having a distal portion adapted to pierce bone and a proximal portion having a head; and (b) a collar comprising: (i) a collar wall defining a cavity and having at least one wall aperture, (ii) a distal portion comprising an opening and a collar seat projecting inward and supporting the head of the bone fastener, (iii) a proximal portion having a non-cammed slot, and (iv) a spinal rod locking device, wherein at least a portion of the spinal rod locking device is within the cavity defined by the collar wall, wherein the bone attachment device further comprises: (a) a collar overhang extending from a proximal portion of the collar toward the cavity; and (b) a washer having a beveled surface at a distal end, wherein the beveled surface abuts a proximal portion of the bone fastener, wherein the spinal rod locking device comprises: (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (d) a clamp member possessing a proximal cam surface, which interacts with the distal cam surface of the nut, and which is adapted to receive distal force from the nut and impart distal force to a rod extending through the wall aperture, and further possessing a distal surface, at least a portion of which is planar, convex or concave, and is adapted to engage the rod extending through the wall aperture. In some embodiments, the non-cammed slot and the overhang are on at least one of an inner surface of the collar and an outer surface of the collar. In some embodiments, the collar engagement member is adapted to cooperate with the non-cammed slot to engage the overhang of the collar to resist proximal motion of the nut, whereby force imparted by turning of the nut about the axis is directed distally. In some embodiments, the beveled surface is planar frustoconical. In some embodiments, the distal surface of the clamp member is concave.

Some embodiments described herein provide a bone attachment device, comprising: (a) a bone fastener having a distal portion adapted to pierce bone and a proximal portion having a head; and (b) a collar comprising: (i) a collar wall defining a cavity and having at least one wall aperture, (ii) a distal portion comprising an opening and a collar seat projecting inward and supporting the head of the bone fastener, (iii) a proximal portion having a non-cammed slot, and (iv) a spinal rod locking device, wherein at least a portion of the spinal rod locking device is within the cavity defined by the collar wall, wherein the bone attachment device, further comprises: (a) a collar overhang extending from a proximal portion of the collar toward the cavity; and (b) a washer having a beveled surface at a distal end, wherein the beveled surface abuts a proximal portion of the head of the bone fastener, wherein the beveled surface is planar frustoconical, wherein the spinal rod locking device comprises: (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (d) a clamp member possessing a proximal cam surface, which interacts with the distal cam surface of the nut, and which is adapted to receive distal force from the nut and impart distal force to a rod extending through the wall aperture, and further possessing a distal surface, at least a portion of which is concave, and is adapted to engage the rod extending through the wall aperture. In some embodiments, the non-cammed slot and the overhang are on at least one of an inner surface of the collar and an outer surface of the collar. In some embodiments, the collar engagement member is adapted to cooperate with the non-cammed slot to engage the overhang of the collar to resist proximal motion of the nut, whereby force imparted by turning of the nut about the axis is directed distally. In some embodiments, the collar seat has a beveled surface, which is planar, convex or concave frustoconical. In some embodiments, the beveled surface is on a distal surface of the collar seat. In some embodiments, the beveled surface is on at least one of a distal portion and a proximal portion of the collar seat.

Some embodiments described herein provide a spinal stabilizer, comprising: (a) at least two bone attachment devices, comprising: (i) a bone fastener having a distal portion adapted to pierce bone and a proximal portion having a head; and (ii) a collar comprising: (A) a collar wall defining a cavity and having at least one wall aperture, (B) a distal portion comprising an opening and a collar seat projecting inward and supporting the head of the bone fastener, (C) a proximal portion having a non-cammed slot, and (D) a spinal rod locking device; and (b) a bone stabilization rod extending through the wall apertures of at least two bone attachment devices, wherein the spinal rod locking devices are adapted to lock the rod in place, thereby preventing translational motion of the rod. In some embodiments, the rod has a substantially uniform cross section. In some embodiments, the cross section is circular, elliptical, or polygonal. In some embodiments, the cross section is circular. In some embodiments, the cross section is polygonal. In some embodiments, the polygonal cross section is triangular, quadrangular (e.g. square, rectangular, rhomboidal, trapezoidal), pentagonal, hexagonal, heptagonal or octagonal. In some embodiments, the bone attachment device further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises a beveled surface. In some embodiments, the beveled surface is on the interior surface of the cylindrical wall. In some embodiments, the beveled surface is concave, convex or planar frustoconical. In some embodiments, the spinal rod locking device comprises a nut. In some embodiments, the nut fits with the cavity. In some embodiments, the nut comprises a cam surface. In some embodiments, the cam surface is on a distal portion of the nut. In some embodiments, the nut further comprises a collar engagement member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the spinal rod locking device comprises a clamp member having a distal surface. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of the rod. In some embodiments, the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a bone attachment device, comprising: (a) a bone fastener having a distal portion adapted to pierce bone and a proximal portion having a head; and (b) a collar comprising: (i) a collar wall defining a cavity and having at least one wall aperture, (ii) a distal portion comprising an opening and a collar seat projecting inward and supporting the head of the bone fastener, (iii) a proximal portion having a non-cammed slot, and (iv) a spinal rod locking device, wherein at least a portion of the spinal rod locking device is within the cavity defined by the collar wall, wherein the spinal rod locking device comprises: (a) a nut; and (b) a clamp member. In some embodiments, the spinal stabilizer of further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises a beveled surface. In some embodiments, the beveled surface is on the interior surface of the cylindrical wall. In some embodiments, the beveled surface is concave, convex or planar. In some embodiments, the proximal portion of the collar comprises an aperture through which the nut projects. In some embodiments, the nut comprises a cam surface. In some embodiments, the cam surface is on a distal portion of the nut. In some embodiments, the nut further comprises a collar engagement member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of the rod. In some embodiments, the collar seat comprises a beveled surface. In some embodiments, the beveled surface faces the distal portion of the collar. In some embodiments, the beveled surface is on at least one of a distal portion and a proximal portion of the collar seat. In some embodiments, the bone attachment device further comprises a washer fitting on the proximal portion of the bone fastener, and wherein the spinal rod locking device comprises: (a) a nut, which is adapted to turn about an axis, and which possesses a distal cam surface, which is adapted to impart distal force to a clamp member; and (b) the clamp member possessing a proximal cam surface, which interacts with the distal cam surface of the nut, and which is adapted to receive distal force from the nut and impart distal force to a rod extending through the wall apertures. In some embodiments, washer possesses a beveled surface. In some embodiments, the beveled surface is on a distal end of the washer. In some embodiments, the beveled surface is convex, concave or planar frustoconical. In some embodiments, the beveled surface is planar frustoconical. In some embodiments, the nut comprises a collar engagement member. In some embodiments, the collar engagement member is adapted to engage an overhang in the collar. In some embodiments, the collar engagement member is adapted to engage the overhang to resist proximal motion of the nut, whereby force imparted by turning of the nut about the axis is directed distally. In some embodiments, the clamp member possesses a planar, concave or convex distal surface adapted to engage a rod extending through the wall apertures. In some embodiments, the clamp member possesses a concave distal surface.

Some embodiments described herein provide a bone attachment device, comprising: (a) a bone fastener having a distal portion adapted to pierce bone and a proximal portion having a head; and (b) a collar comprising: (i) a collar wall defining a cavity and having at least one wall aperture, (ii) a distal portion comprising an opening and a collar seat projecting inward and supporting the head of the bone fastener, (iii) a proximal portion having a non-cammed slot, and (iv) a spinal rod locking device, wherein at least a portion of the spinal rod locking device is within the cavity defined by the collar wall, wherein the bone attachment device further comprises: (a) a collar overhang extending from a proximal portion of the collar toward the cavity; and (b) a washer having a beveled surface at a distal end, wherein the beveled surface abuts a proximal portion of the bone fastener, and wherein the spinal rod locking device comprises: (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (d) a clamp member possessing a proximal cam surface, which interacts with the distal cam surface of the nut, and which is adapted to receive distal force from the nut and impart distal force to a rod extending through the wall apertures, and further possessing a distal surface, at least a portion of which is planar, convex or concave, and is adapted to engage the rod extending through the wall apertures. In some embodiments, the collar engagement member is adapted to cooperate with the non-cammed slot to engage the overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the beveled surface is planar frustoconical. In some embodiments, the distal surface of the clamp member is concave.

Some embodiments described herein provide a bone attachment device, comprising: (a) a bone fastener having a distal portion adapted to pierce bone and a proximal portion having a head; and (b) a collar comprising: (i) a collar wall defining a cavity and having at least one wall aperture, (ii) a distal portion comprising an opening and a collar seat projecting inward and supporting the head of the bone fastener, (iii) a proximal portion having a non-cammed slot, and (iv) a spinal rod locking device, wherein at least a portion of the spinal rod locking device is within the cavity defined by the collar wall, wherein the bone attachment device further comprises: (a) a collar overhang extending from a proximal portion of the collar toward the cavity; and (b) a washer having a beveled surface at a distal end, wherein the beveled surface abuts a proximal portion of the bone fastener, wherein the beveled surface is planar frustoconical, and wherein the spinal rod locking device comprises: (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (d) a clamp member possessing a proximal cam surface, which interacts with the distal cam surface of the nut, and which is adapted to receive distal force from the nut and impart distal force to a rod extending through the wall apertures, and further possessing a distal surface, at least a portion of which is concave, and is adapted to engage the rod extending through the wall aperture. In some embodiments, the collar engagement member is adapted to cooperate with the non-cammed slot to engage the overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the collar seat has a beveled surface, which is planar, convex or concave frustoconical. In some embodiments, the beveled surface is on at least one of a distal portion and a proximal portion of the collar seat. In some embodiments, the spinal rod locking devices are adapted to lock the orientation of the bone fastener relative to the rod when the rod is locked in place.

Some embodiments described herein provide a bone attachment collar, comprising: (a) a collar wall defining a cavity and having at least one wall aperture; (b) a distal portion comprising an opening and a collar seat projecting inward and supporting the head of a bone fastener; (c) a proximal portion having a non-cammed slot; and (d) a spinal rod locking device, wherein at least a portion of the spinal rod locking device is within the cavity defined by the collar wall. In some embodiments, the bone attachment collar further comprises a washer. In some embodiments, the washer comprises a substantially cylindrical wall having an interior surface and an exterior surface; and the washer has a proximal end and a distal end. In some embodiments, the distal end of the washer is adapted to fit over a proximal portion of a bone fastener. In some embodiments, the distal end of the washer comprises a beveled surface. In some embodiments, the beveled surface is on the interior surface of the cylindrical wall. In some embodiments, the beveled surface is concave, convex or planar. In some embodiments, the spinal rod locking device comprises a nut. In some embodiments, the nut fits with the cavity. In some embodiments, the nut comprises a cam surface. In some embodiments, the cam surface is on a distal portion of the nut. In some embodiments, the nut further comprises a collar engagement member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the spinal rod locking device comprises a clamp member having a distal surface. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of a rod extending through the wall apertures. In some embodiments, the collar seat comprises a beveled surface. In some embodiments, the beveled surface faces the distal portion of the collar. In some embodiments, the beveled surface is on at least one of a distal portion and a proximal portion of the collar seat.

Some embodiments described herein provide a bone attachment collar, comprising: (a) a collar wall defining a cavity and having at least one wall aperture; (b) a distal portion comprising an opening and a collar seat projecting inward and supporting the head of a bone fastener; (c) a proximal portion having a non-cammed slot; and (d) a spinal rod locking device, wherein at least a portion of the spinal rod locking device is within the cavity defined by the collar wall, wherein the spinal rod locking device comprises: (a) a nut; and (b) a clamp member. In some embodiments, the bone attachment collar further comprises a washer. In some embodiments, the washer comprises a substantially cylindrical wall having an interior surface and an exterior surface; and the washer has a proximal end and a distal end. In some embodiments, the distal end of the washer fits over the head of the bone fastener. In some embodiments, the distal end of the washer comprises beveled surface. In some embodiments, the beveled surface is on the interior surface of the cylindrical wall. In some embodiments, the beveled surface is concave, convex or planar. In some embodiments, the proximal portion of the collar comprises an aperture through which the nut projects. In some embodiments, the nut comprises a cam surface. In some embodiments, the cam surface is on a distal portion of the nut. In some embodiments, the nut further comprises a collar engagement member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the clamp member comprises a cam surface. In some embodiments, the cam surface is on a proximal end of the clamp member. In some embodiments, the cam surface on the proximal end of the clamp member is adapted to engage the cam surface on the distal portion of the nut, whereby turning the nut imparts distal force to the clamp member. In some embodiments, at least a portion of a distal surface of the clamp member is concave, convex or planar. In some embodiments, at least a portion of the distal surface of the clamp member is concave. In some embodiments, the surface is adapted to engage a surface of a rod extending through the wall apertures. In some embodiments, the collar seat comprises a beveled surface. In some embodiments, the beveled surface faces the distal portion of the collar. In some embodiments, the beveled surface is on at least one of a distal portion and a proximal portion of the collar seat. In some embodiments, the bone attachment collar further comprises a washer fitting on the proximal portion of the bone fastener, wherein the spinal rod locking device comprises: (a) a nut, which is adapted to turn about an axis, and which possesses a distal cam surface, which is adapted to impart distal force to a clamp member; and (b) the clamp member possessing a proximal cam surface, which interacts with the distal cam surface of the nut, and which is adapted to receive distal force from the nut and impart distal force to a rod extending through the wall apertures. In some embodiments, the washer possesses a beveled surface. In some embodiments, the beveled surface is on a distal end of the washer. In some embodiments, the beveled surface is convex, concave or planar frustoconical. In some embodiments, the beveled surface is planar frustoconical. In some embodiments, the nut comprises a collar engagement member. In some embodiments, the collar engagement member is adapted to engage an overhang in the collar. In some embodiments, the non-cammed slot and the overhang are on at least one of an inner surface of the collar and an outer surface of the collar. In some embodiments, the collar engagement member is adapted to engage the overhang to resist proximal motion of the nut, whereby force imparted by turning of the nut about the axis is directed distally. In some embodiments, the clamp member possesses a planar, concave or convex distal surface adapted to engage a rod extending through the wall apertures. In some embodiments, the clamp member possesses a concave distal surface.

Some embodiments described herein provide a bone attachment collar, comprising: (a) a collar wall defining a cavity and having at least one wall aperture; (b) a distal portion comprising an opening and a collar seat projecting inward and supporting the head of a bone fastener; (c) a proximal portion having a non-cammed slot; and (d) a spinal rod locking device, wherein at least a portion of the spinal rod locking device is within the cavity defined by the collar wall, wherein the bone attachment collar further comprises: (a) a collar overhang extending from a proximal portion of the collar toward the cavity; and (b) a washer having a beveled surface at a distal end, wherein the beveled surface abuts a proximal portion of the bone fastener, and wherein the spinal rod locking device comprises: (c) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (d) a clamp member possessing a proximal cam surface, which interacts with the distal cam surface of the nut, and which is adapted to receive distal force from the nut and impart distal force to a rod extending through the wall apertures, and further possessing a distal surface, at least a portion of which is planar, convex or concave, and is adapted to engage the rod extending through the wall aperture. In some embodiments, the collar engagement member is adapted to cooperate with the non-cammed slot to engage the overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the beveled surface is planar frustoconical. In some embodiments, the distal surface of the clamp member is concave. In some embodiments, the bone attachment collar further comprises: (a) a collar overhang extending from a proximal portion of the collar toward an axis; and (b) a washer having a beveled surface at a distal end, wherein the beveled surface abuts a proximal portion of the bone fastener, wherein the beveled surface is planar frustoconical, and, wherein the spinal rod locking device comprises: (i) a nut, which is adapted to turn about an axis, and which possesses a distal cam surface, which is adapted to impart distal force to a clamp member, wherein the nut further comprises a collar engagement member, which is adapted to engage the collar overhang, whereby force imparted by turning the nut about the axis is directed distally; and (ii) a clamp member possessing a proximal cam surface, which interacts with the distal cam surface of the nut, and which is adapted to receive distal force from the nut and impart distal force to a rod extending through the wall apertures, and further possessing a distal surface, at least a portion of which is concave, and is adapted to engage the rod extending through the wall apertures. In some embodiments, the collar engagement member is adapted to cooperate with the non-cammed slot to engage the overhang of the collar to resist proximal motion of the nut, whereby force imparted by turning of the nut about the axis is directed distally. In some embodiments, the non-cammed slot and the overhang are on at least one of an inner surface of the collar and an outer surface of the collar. In some embodiments, the collar seat has a beveled surface, which is planar, convex or concave frustoconical. In some embodiments, the beveled surface is on at least one of a distal portion and a proximal portion of the collar seat.

Some embodiments described herein provide a method for implanting a spinal stabilization device comprising: (a) delivering a first bone attachment device to a first pedicle, wherein the first bone attachment device comprises: (i) a first bone fastener having a distal portion adapted to pierce bone and a proximal portion having a head, and (ii) a first collar comprising: (A) a collar wall defining a cavity and having at least one wall aperture; (B) a distal portion comprising an opening and a collar seat projecting inward and supporting a head of the bone fastener; (C) a proximal portion having a hinged lid; and (D) a spinal rod locking device, wherein at least a portion of the spinal rod locking device is within the cavity defined by the collar wall; (b) fastening the distal portion of the first bone fastener to the first pedicle; (c) delivering a second bone attachment device to a second pedicle, wherein the second bone attachment device comprises (i) a second bone fastener having a distal portion adapted to pierce bone and a proximal portion having a head, and (ii) a second collar comprising: (A) a collar wall defining a cavity and having at least one wall aperture; (B) a distal portion comprising an opening and a collar seat projecting inward and supporting a head of the bone fastener; and (C) a spinal rod locking device, wherein at least a portion of the spinal rod locking device is within the cavity defined by the collar wall; (d) placing a rod within the aperture of the first bone attachment device; (e) placing the rod within the aperture of the second bone attachment device; (f) locking the first bone attachment device, wherein the locking comprises: (i) pivoting the hinged lid toward the first collar over the rod, and (ii) engaging an overhang of the first collar with a collar engagement member of the spinal rod locking device of the first collar; and (g) locking the second bone attachment device, wherein the locking steps lock the rod in place, thereby preventing translational motion of the rod. In some embodiments, the second collar of the second bone attachment device comprises a proximal portion having a hinged lid and wherein locking the second bone attachment device comprises: (a) pivoting the hinged lid toward the first collar over the rod; and (b) engaging an overhang of the first collar with a collar engagement member of the spinal rod locking device of the first collar.

Figure 1B:
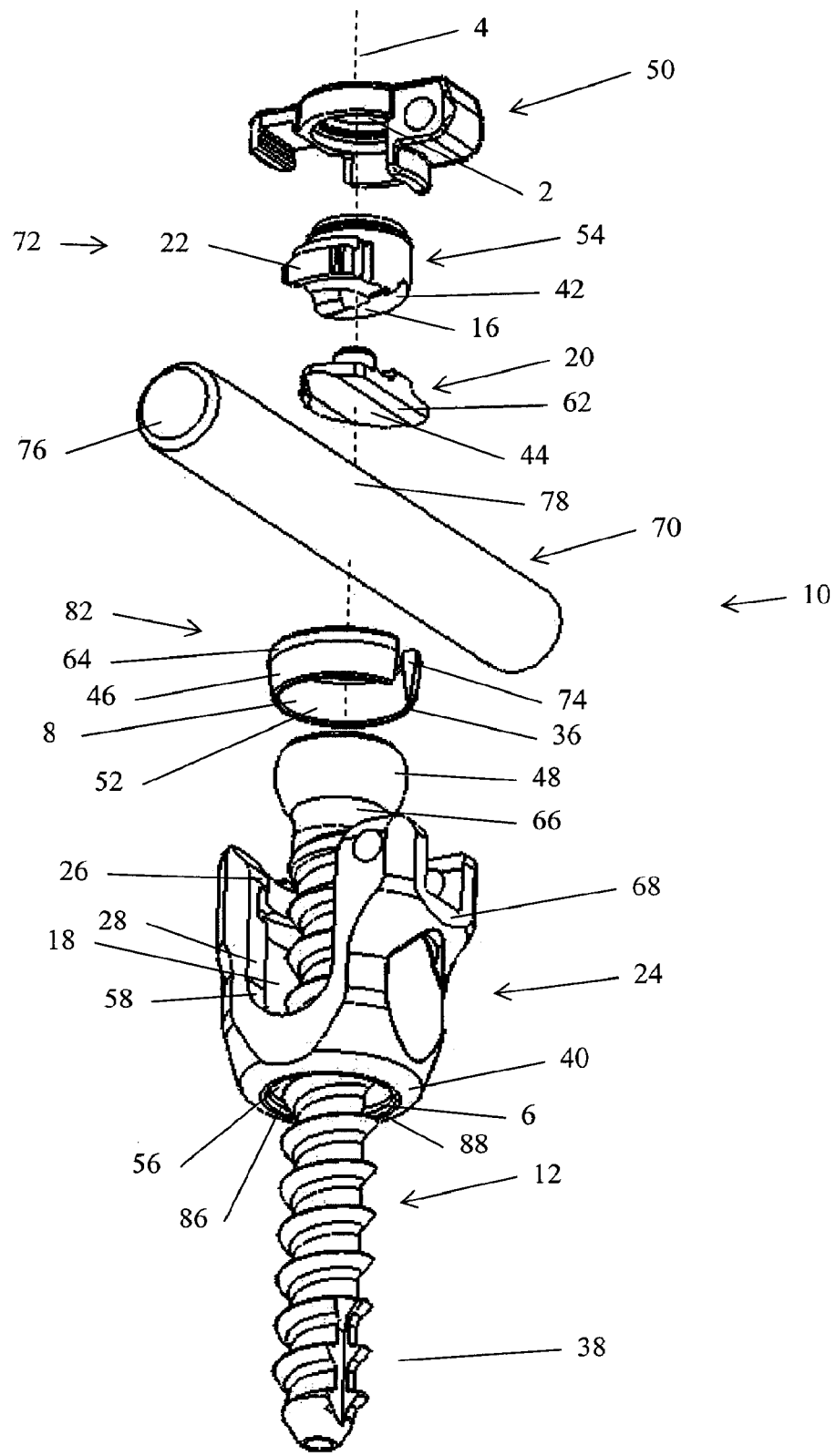
FIG. 1B shows an exploded view of an embodiment of a hinged bone attachment device including a rod.

FIG. 1A and FIG. 1B depict an illustrative embodiment of a bone attachment device 10 comprising a bone fastener 12 having a distal portion 38 adapted to pierce bone and a proximal portion 66 having a head 48. In some embodiments, the bone attachment device 10 comprises a collar 24 comprising: a collar wall 28 defining a cavity 18 and having at least one wall aperture 58; a distal portion 40 comprising an opening 56 and a collar seat 86 projecting inward and supporting the head 48 of the bone fastener 12; a proximal portion 68 having a hinged lid 50; and a spinal rod locking device 72, wherein at least a portion of the spinal rod locking device 72 is within the cavity 18 defined by the collar wall 28. In some embodiments, the hinged lid 50 attaches to the collar wall 28 with a pivot pin 84. The distal portion 38 of the bone fastener 12 fits through out an opening 56 in the distal portion 40 of the collar 24.

In some embodiments, the bone attachment device comprises a washer 82. The washer 82 has a proximal end 64 and a distal end 36. The washer 82 may comprise a substantially cylindrical wall 74 having an interior surface 52 and an exterior surface 46. In some embodiments, the distal end 36 of the washer 82 fits over the head 48 of the bone fastener 12. The washer 82 may comprise a beveled surface 8. The beveled surface 8 may be on the distal end 36 of the washer 82. The beveled surface 8 may be on the interior surface 52 of the cylindrical wall 74, in some embodiments. The beveled surface 8 may be concave, convex or planar. In some embodiments, the beveled surface 8 is planar frustoconical. In some embodiments, the beveled surface 8 abuts a proximal portion 66 of the bone fastener 12. In some embodiments, the washer 82 fits on the proximal portion 66 of the bone fastener 12.

In some embodiments, the spinal rod locking device 72 comprises a nut 54. The nut 54 may project through an aperture 2 of the hinged lid 50 of the bone attachment device 10. In some embodiments, the nut 54 comprises a cam surface 16. The cam surface 16 may be on a distal portion 42 of the nut 54. In some embodiments, the cam surface 16 is adapted to impart distal force to a clamp member 20 of the spinal rod locking device 72. In some embodiments, the nut 54 is adapted to turn about an axis 4.

The nut 54 may comprise a collar engagement member 22. In some embodiments, the collar engagement member 22 is adapted to engage an inner surface of the collar 24. In some embodiments, the collar engagement member 22 is adapted to engage an outer surface of the collar 24. In some embodiments, the collar engagement member 22 is adapted to engage an overhang 26 in the collar 24. In some embodiments, the overhang 26 is on at least one of an inner surface of the collar 24 and an outer surface of the collar 24. In some embodiments, the collar engagement member 22 is adapted to engage the overhang 26 to resist proximal motion of the nut 54, whereby force imparted by turning of the nut 54 about the axis 4 is directed distally. In some embodiments, the nut 54 is adapted to turn about an axis 4, and possesses a distal cam surface 54, which is adapted to impart distal force to a clamp member 20.

In some embodiments, the spinal rod locking device 72 comprises a clamp member 20 having a distal surface 44. The clamp member 20 may comprise a cam surface 14. The cam surface 14 may be on a proximal end 62 of the clamp member 20. In some embodiments, the cam surface 14 on the proximal end 62 of the clamp member 20 is adapted to engage or interact with the cam surface 16 on the distal portion 42 of the nut 54, whereby turning the nut 54 imparts distal force to the clamp member 20. In some embodiments, at least a portion of the distal surface 44 of the clamp member 20 is concave, convex, or planar. In some embodiments, at least a portion of the distal surface 44 of the clamp member 20 is concave. In some embodiments, the surface 44 is adapted to engage a surface 78 of a rod 70 extending through the wall aperture 58. In some embodiments, the planar, concave, or convex distal surface 44 is adapted to engage the rod 70 extending through the wall aperture 58. The rod 70 is shown in FIG. 1A and FIG. 1B having a substantially uniform cross-section 76. In some embodiments, the clamp member 20 possesses a concave distal surface 44. In some embodiments, the clamp member 20 possesses a proximal cam surface 14 which interacts with the distal cam surface 16 of the nut 54, and which is adapted to receive distal force from the nut 54 and impart distal force to a rod 70 extending through the wall aperture 58.

In some embodiments, the collar seat 86 comprises a beveled surface 6. In some embodiments, the beveled surface 6 faces the distal portion 40 of the collar 24. In some embodiments, the beveled surface 6 is planar, convex or concave frustoconical. In some embodiments, the beveled surface 6 is on a distal portion (not shown) of the collar seat 86. In some embodiments, the beveled surface 6 is on a proximal portion 90 of the collar seat 86.

In some embodiments, the bone attachment device 10 comprises a collar overhang 26 extending from a portion of the collar 24 toward the cavity 18. In some embodiments, the overhang 26 is on at least one of an inner surface of the collar 24 and an outer surface of the collar 24.

The hinged bone attachment device 210, 310, 410, has at least three positions: (1) open, depicted in FIG. 2, (2) closed and unlocked, an embodiment depicted in FIG. 3 and FIG. 4, and (3) closed and locked, an embodiment depicted in FIG. 5 and FIG. 6. The bone attachment device 210, 310, 410, 510, 610 is capable, at least, of movement between each of these positions by pivoting the hinged lid 250, 350, 450, 550, 650 with the spinal rod locking device 272, 372, 472, 572, 672 engaged against the hinged lid 250, 350, 450, 550, 650 about the pivot pin 284, 384, 484, 584, 684 which defines a pivot axis for the hinged lid 250, 350, 450, 550, 650.

Figure 2:
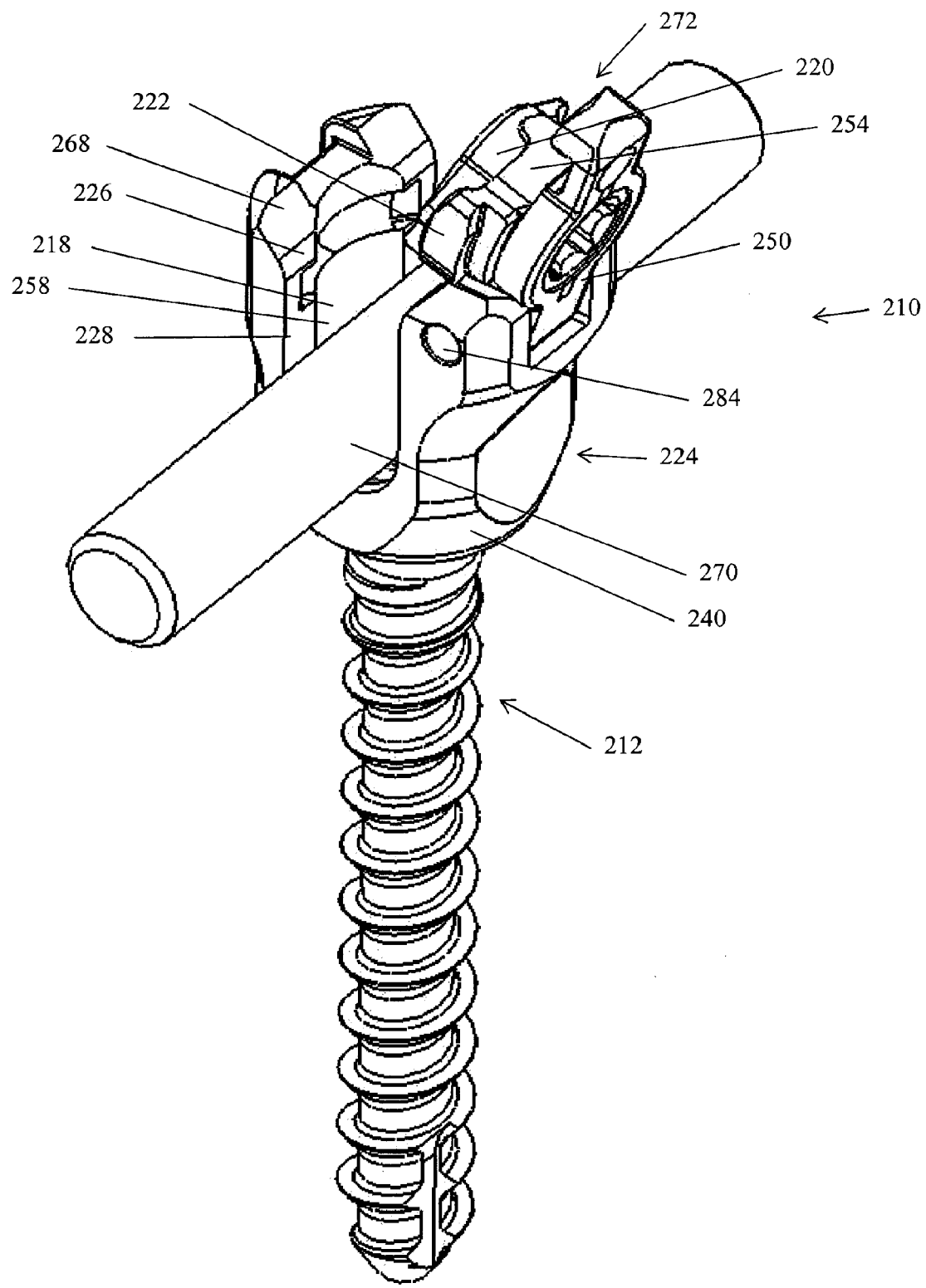
FIG. 2 depicts an embodiment of a hinged bone attachment device, including a rod, which is closed and unlocked.

Thus, depicted in FIG. 2 is an open embodiment of a hinged bone attachment device 210 including a rod 270. With the hinged lid 250 and the spinal rod locking device 272 open, the rod 270 can be placed into the cavity 218 defined by the collar wall 228 of the collar 224, and through at least one wall aperture 258 of the collar 224. Once placed into the cavity 218, the rod 270 rests against the washer (not shown) within the cavity 218 of the collar 224, which engages the head (not shown) of the bone fastener 212. FIG. 2 also shows an embodiment of the bone attachment collar 224 having a distal portion 240, a proximal portion 268, and an overhang 226. The overhang 226 can be used in conjunction with the spinal rod locking device 272 to lock the rod 270 against translation and into a fixed orientation relative to the bone fastener 212. In some embodiments, spinal rod locking device 272 of the bone attachment device 210 is adapted to lock the rod 270 in place, thereby preventing translational motion of the rod 270. In some embodiments, spinal rod locking device 272 of the bone attachment device 210 is adapted to lock the orientation of the bone fastener 212 relative to the rod 270 when the rod 270 is locked in place.

The spinal rod locking device 272 depicted in FIG. 2 comprises a clamp member 220 which is adapted to engage the surface of the rod 270 when the bone attachment device 210 is closed and unlocked, and/or closed and locked. At least a portion of the proximal end (not shown) of the clamp member 220 engages the nut 254. Both the nut 254 and the clamp member 220, in some embodiments, have cam surfaces (not shown), which face each other. The nut 254, which is capable of rotating within the hinged lid 250, also comprises a collar engagement member 222 which is capable of engaging the collar overhang 226 when the hinged lid 250 and spinal rod locking device 272 are closed and the nut 254 is rotated. In some embodiments, the overhang 226 is on at least one of an inner surface of the collar 224 and an outer surface of the collar 224.

Figure 3:
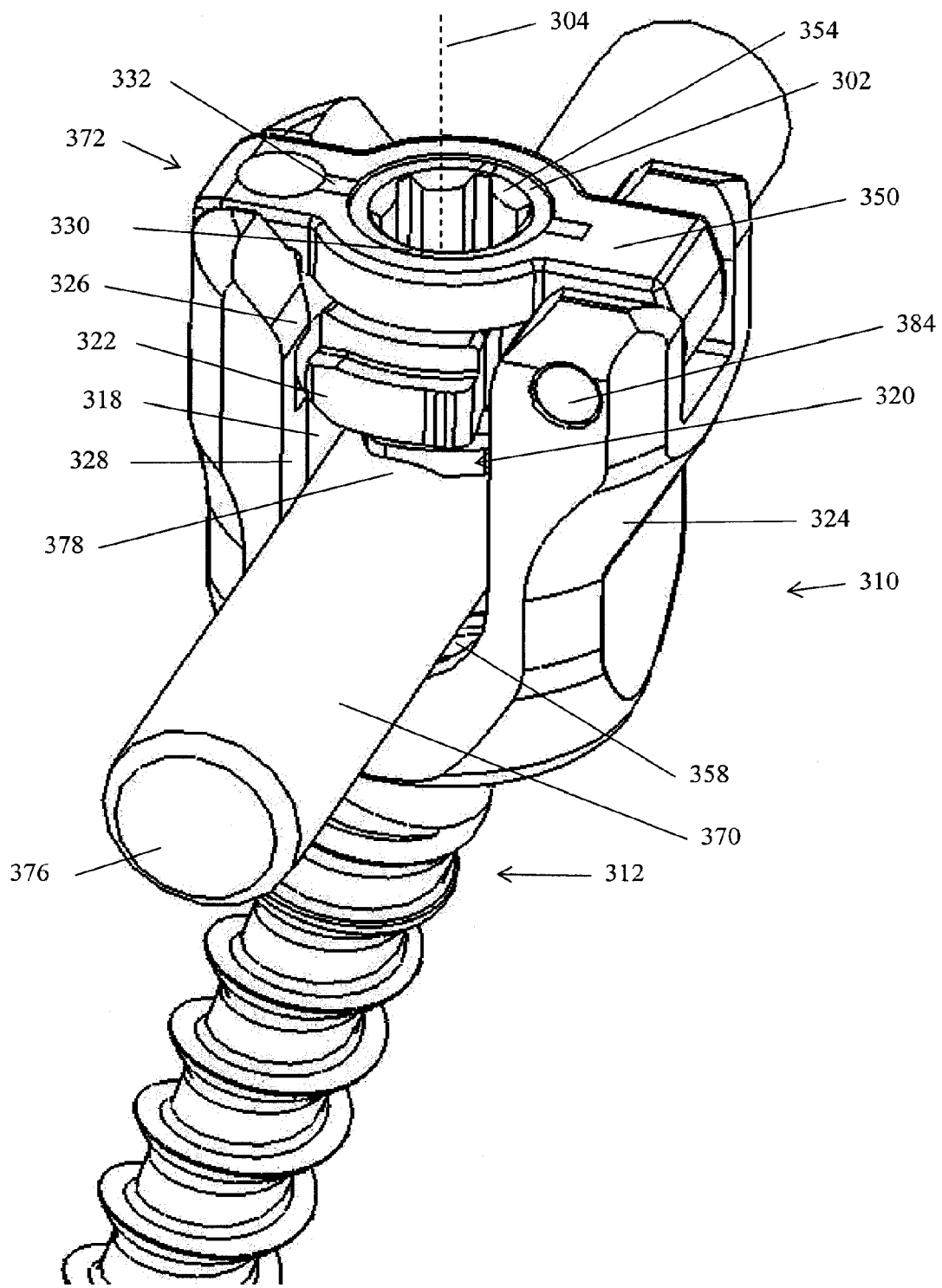
FIG. 3 depicts an embodiment of a hinged bone attachment device, including a rod, is closed and unlocked.

Depicted in FIG. 3 is a closed and unlocked embodiment of the hinged bone attachment device 310 including a rod 370. The polyaxial nature of the bone fastener 312 is shown as the bone fastener is not aligned with the axis 304 about which the nut 354 of the spinal rod locking device 372 is adapted to turn. In this figure, the rod 370 has been placed into the cavity 318 defined by the collar wall 328 of the collar 324, and through at least one wall aperture 358 of the collar 324. The hinged lid 350 and the spinal rod locking device 372 have been pivoted about the pivot pin 384 and the clamp member 320 engages the surface 378 of the rod 370, which has a substantially uniform cross-section 376 (circular in the FIG. 3 embodiment). When the hinged lid 350 and the spinal rod locking device 372 are closed and unlocked, the collar engagement member 322 of the nut 354, is over the rod 370. In this embodiment, the nut 354 is within the aperture 302 of the hinged lid 350, and can be rotated relative to the lid 350 and relative to the clamp member 320. In the unlocked position, the collar engagement member 322 of the nut 354 does not engage the collar overhang 326. From the closed and unlocked position depicted in FIG. 3, the nut 354 may be turned in a clockwise direction such that the nut engagement marking 330 rotates to align with the hinged lid engagement marking 332.

In some embodiments, the collar engagement member 322, and the cam surfaces (not shown) of the nut 354 and the clamp member 320 are positioned and oriented such that counter-clockwise rotation of the nut 354 locks the bone attachment device 310 and rod 370. While the collar overhang 326 depicted in FIG. 3 is in the collar wall 328 on the opposite side of the cavity 318 to the pivot pin 384, in some embodiments, the overhang 326 is in wall 328 on the same side of the cavity 318 as the pivot pin 384. In some embodiments, the overhang 326 is on at least one of an inner surface of the collar 324 and an outer surface of the collar 324.

In some embodiments, the lid 350 comprises a lid hook (not shown), which hooks the collar 324 on the opposite side of the cavity 318 to the pivot pin 384. This hook may temporarily and/or loosely fix the position and orientation of the bone attachment device 310 and rod 370 relative to the bone fastener 312. The collar may additionally comprise a hook engagement member (not shown) which facilitates temporarily and/or loosely fixing the position and orientation of the bone attachment device 310 and rod 370 relative to the bone fastener 312 when the hook engagement member is engaged by the hook of the lid 350.

Figure 4:
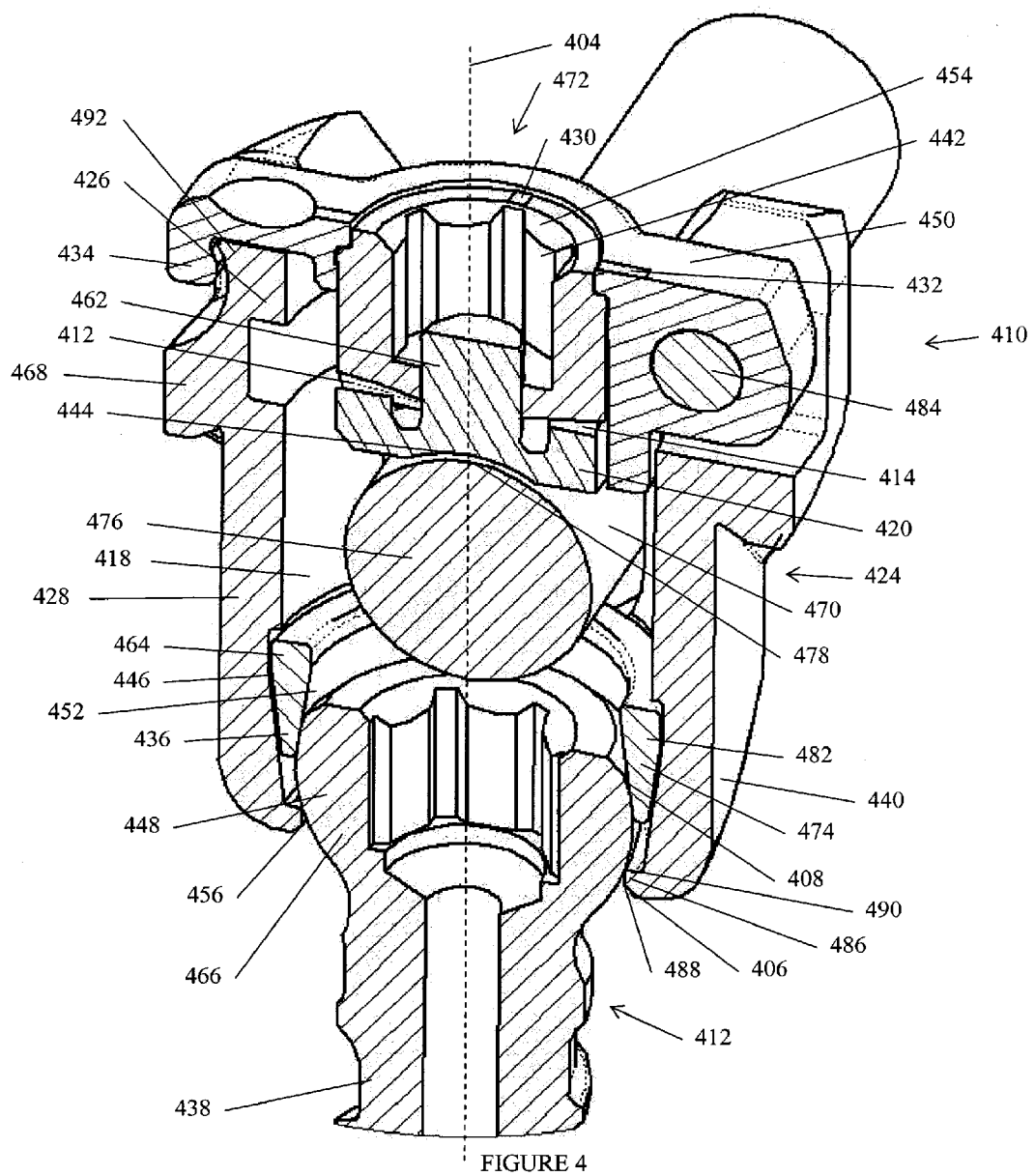
FIG. 4 depicts a cross-section view of an embodiment of a hinged bone attachment device, including a rod, which is closed and unlocked.

Depicted in FIG. 4 is a cross-section view of the closed and unlocked embodiment of the hinged bone attachment device of FIG. 4 including a rod. In this figure, bone fastener 412 has been placed through the cavity 418 of the collar 424. The head 448 of the bone fastener 412 rests against the collar seat 486. The washer 482 has been placed against the head 448 of the bone fastener 412 and within the cavity 418 of the collar 424. The beveled surface 408 of the distal end 436 of the washer 482 contacts the head 448 of the bone fastener 412. The rod 470 has been placed into the cavity 418 defined by the collar wall 428 of the collar 424, and through at least one wall aperture 458 of the collar 424. The rod 470 rests on the washer 482. The hinged lid 450 and the spinal rod locking device 472 have been pivoted about the pivot pin 484 and the clamp member 420 engages the surface 478 of the rod 470, which has a substantially uniform cross-section 476 (circular in the FIG. 4 embodiment). When the hinged lid 450 and the spinal rod locking device 472 are closed and unlocked, the collar engagement member (not shown) of the nut 454, is over the rod 470. In this embodiment, the nut 454 is within the aperture 402 of the hinged lid 450, and can be rotated relative to the lid 450 and relative to the clamp member 420. In the unlocked position, the collar engagement member (not shown) of the nut 454 does not engage the collar overhang 426. In some embodiments, the overhang 426 is on at least one of an inner surface of the collar 424 and an outer surface of the collar 424. From the closed and unlocked position depicted in FIG. 4, the nut 454 may be turned in a clockwise direction such that the nut engagement marking 430 rotates to align with the hinged lid engagement marking 432. In some embodiments, the collar engagement member 422, and the cam surface 412 of the nut 454 and the cam surface 414 of the clamp member 420 are positioned and oriented such that clockwise rotation of the nut 454 locks the bone attachment device 410 and rod 470. In the embodiment of FIG. 4, the cam surface 412 of the nut 454 and the cam surface 414 of the clamp member 420 face each other, such that when the nut 454 is turned clockwise, rotation of the nut 454 locks the bone attachment device 410 and rod 470.

In some embodiments, the collar engagement member 422, and the cam surface 412 of the nut 454 and the cam surface 414 of the clamp member 420 are positioned and oriented such that counter-clockwise rotation of the nut 454 locks the bone attachment device 410 and rod 470. While the collar overhang 426 depicted in FIG. 4 is in the collar wall 428 on the opposite side of the cavity 418 to the pivot pin 484, in some embodiments, the overhang 426 is in wall 428 on the same side of the cavity 418 as the pivot pin 484. In some embodiments, the overhang 426 is on at least one of an inner surface of the collar 424 and an outer surface of the collar 424.

In some embodiments, and shown in FIG. 4, the lid 450 comprises a lid hook 434, which hooks the collar 424 on the opposite side of the cavity 418 from the pivot pin 484. This hook may temporarily and/or loosely fix the position and orientation of the bone attachment device 410 and rod 470 relative to the bone fastener 412 before turning the nut 454 to lock the rod 470 from translation and position of the collar 424 relative to the rod 470 and bone fastener 412. In some embodiments, spinal rod locking device 472 of the bone attachment device 410 is adapted to lock the rod 470 in place, thereby preventing translational motion of the rod 470. In some embodiments, spinal rod locking device 472 of the bone attachment device 410 is adapted to lock the orientation of the bone fastener 412 relative to the rod 470 when the rod 470 is locked in place. The collar may additionally comprise a hook engagement member 492 which facilitates temporarily and/or loosely fixing the position and orientation of the bone attachment device 410 and rod 470 relative to the bone fastener 412 when the hook engagement member 492 is engaged by the hook of the lid 450.

Figure 5:
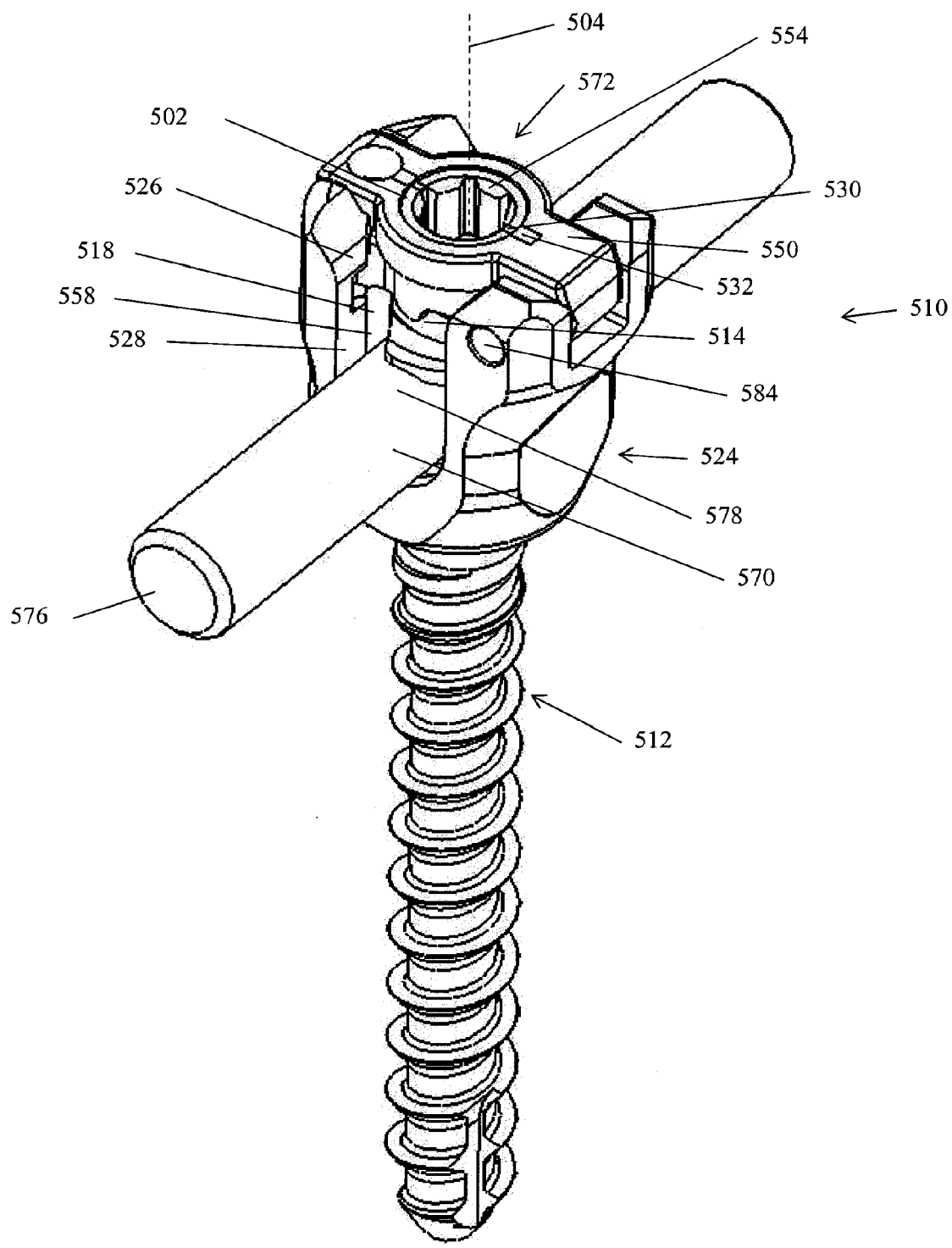
FIG. 5 shows an embodiment of a hinged bone attachment device, including a rod, which is closed and locked.

Depicted in FIG. 5 is a closed and locked embodiment of the hinged bone attachment device 510 including a rod 570. In the closed and locked position, the rod 570 has been placed into the cavity 518 defined by the collar wall 528 of the collar 524, and through at least one wall aperture 558 of the collar 524. The hinged lid 550 and the spinal rod locking device 572 have been pivoted about the pivot pin 584 and the clamp member 520 engages the surface 578 of the rod 570, which has a substantially uniform cross-section 576 (circular in the FIG. 5 embodiment). The nut 554 is within the aperture 502 of the hinged lid 550, and has been rotated in a clockwise direction relative to the lid 550 and relative to the clamp member 520, such that the collar engagement member (not shown) of the nut 554, engages the collar overhang 526, and the cam surfaces (not shown) of the nut 554 and the clamp member 520 cam against one another. In the embodiment depicted in FIG. 5, the overhang 526 is on the inner surface of the collar 524. In some embodiments, the overhang 226 is on an outer surface of the collar 224. The rotational force of turning the nut 554 about the axis 504, translates rotational motion into axial motion, and moves at least the clamp member 520 distally along axis 504. This locks the rod 570 from translation along its length and locks the position and orientation of the collar 524 relative to the bone fastener 512. In the embodiment shown in FIG. 5, the bone attachment device 510 is fully locked at least when the nut 554 is turned such that the nut engagement marking 530 aligns with the hinged lid engagement marking 532.

Figure 6:
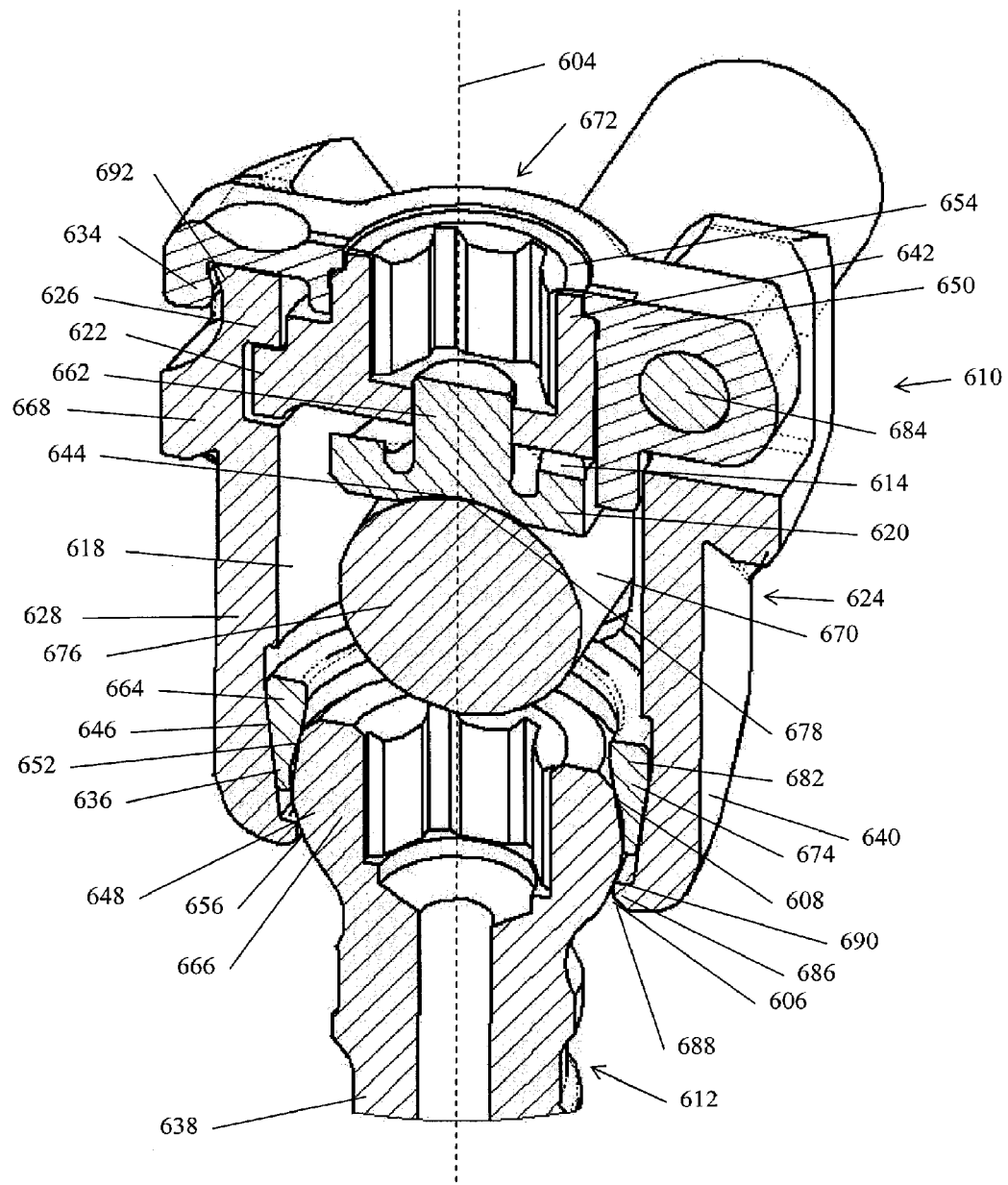
FIG. 6 depicts a cross-section view of an embodiment of a hinged bone attachment device, including a rod, which is closed and locked.

FIG. 6 depicts a cross-section view of the closed and locked embodiment of the hinged bone attachment device of FIG. 5 including a rod. In this figure, bone fastener 612 has been placed through the cavity 618 of the collar 624. The head 648 of the bone fastener 612 rests against the collar seat 686. The washer 682 has been placed against the head 648 of the bone fastener 612 and within the cavity 618 of the collar 624. The beveled surface 608 of the distal end 636 of the washer 682 contacts the head 648 of the bone fastener 612. The rod 670 has been placed into the cavity 618 defined by the collar wall 628 of the collar 624, and through at least one wall aperture 658 of the collar 624. The rod 670 rests on the washer 682. The hinged lid 650 and the spinal rod locking device 672 have been pivoted about the pivot pin 684 and the clamp member 620 engages the surface 678 of the rod 670, which has a substantially uniform cross-section 676 (circular in the FIG. 6 embodiment).

In some embodiments, and shown in FIG. 6, the lid 650 comprises a lid hook 634, which hooks the collar 624 on the opposite side of the cavity 618 from the pivot pin 684. This hook may temporarily and/or loosely fix the position and orientation of the bone attachment device 610 and rod 670 relative to the bone fastener 612 before turning the nut 654 to lock the rod 670 from translation and position of the collar 624 relative to the rod 670 and bone fastener 612. In some embodiments, spinal rod locking device 672 of the bone attachment device 610 is adapted to lock the rod 670 in place, thereby preventing translational motion of the rod 670. In some embodiments, spinal rod locking device 672 of the bone attachment device 610 is adapted to lock the orientation of the bone fastener 612 relative to the rod 670 when the rod 670 is locked in place. The collar may additionally comprise a hook engagement member 692 which facilitates temporarily and/or loosely fixing the position and orientation of the bone attachment device 610 and rod 670 relative to the bone fastener 612 when the hook engagement member is engaged by the hook of the lid 650.

In FIG. 6, the nut 654 is within the aperture 602 of the hinged lid 650, and has been rotated in a clockwise direction relative to the lid 650 and relative to the clamp member 620, such that the collar engagement member 622 of the nut 654, engages the collar overhang 626, and the cam surface (not shown) of the nut 654 and the cam surface 614 of the clamp member 620 cam against one another. The rotational force of turning the nut 654 about the axis 604, translates rotational motion into axial motion, and at least moves the clamp member 620 distally along axis 604. This locks the rod 670 from translation along its length and locks the position and orientation of the collar 624 relative to the bone fastener 612. In the embodiment shown in FIG. 6, the bone attachment device 610 is sufficiently locked at least when the nut 654 is turned such that the nut engagement marking 630 aligns with the hinged lid engagement marking 632. In the embodiment depicted in FIG. 6, the overhang 626 is on the inner surface of the collar 624. In some embodiments, the overhang 626 is on an outer surface of the collar 624.

Figure 7A:
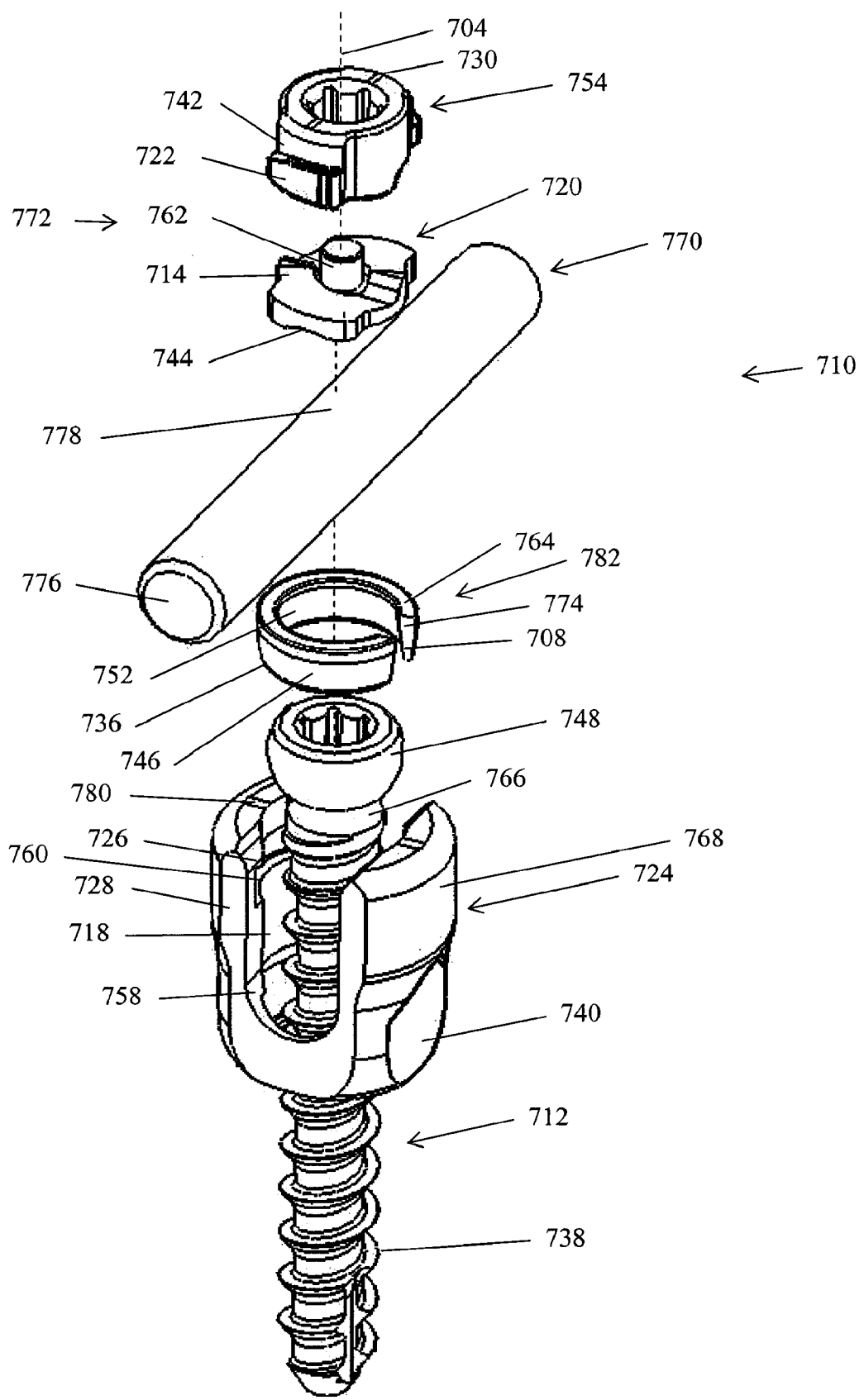
FIG. 7A shows an exploded view of an embodiment of a non-hinged bone attachment device including a rod.
Figure 7B:
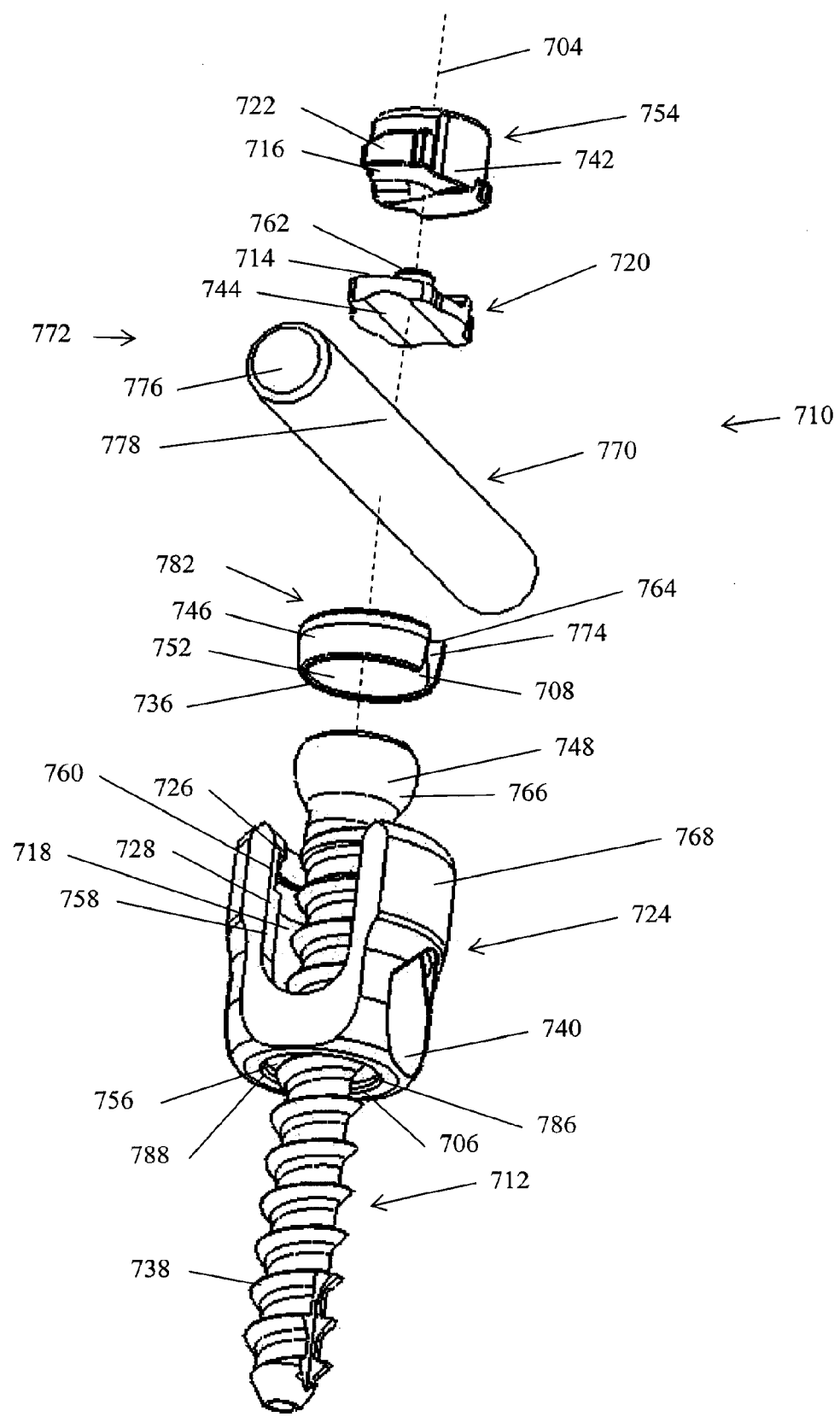
FIG. 7B depicts an exploded view of an embodiment of a non-hinged bone attachment device including a rod.

Provided herein and depicted in FIG. 7A and FIG. 7B is an embodiment of a bone attachment device 710 comprising a bone fastener 712 having a distal portion 738 adapted to pierce bone and a proximal portion 766 having a head 748. In some embodiments, the bone attachment device 710 comprises a collar 724 comprising: a collar wall 28 defining a cavity 718 and having at least one wall aperture 758; a distal portion 740 comprising an opening 756 and a collar seat 786 projecting inward and supporting the head 748 of the bone fastener 712; a proximal portion 768 having a non-cammed slot 760, and a spinal rod locking device 772, wherein at least a portion of the spinal rod locking device 772 is within the cavity 718 defined by the collar wall 728. The distal portion 38 of the bone fastener 712 fits through out an opening 756 in the distal portion 740 of the collar 724.

In some embodiments, the bone attachment device 710 comprises a washer 782. The washer 782 has a proximal end 764 and a distal end 736. The washer 782 may comprise a substantially cylindrical wall 774 having an interior surface 752 and an exterior surface 746. In some embodiments, the distal end 736 of the washer 782 fits over the head 748 of the bone fastener 712. The washer 782 may comprise a beveled surface 708. The beveled surface 78 may be on the distal end 736 of the washer 782. The beveled surface 708 may be on the interior surface 752 of the cylindrical wall 774, in some embodiments. The beveled surface 708 may be concave, convex or planar. In some embodiments, the beveled surface 708 is planar frustoconical. In some embodiments, the beveled surface 708 abuts a proximal portion 766 of the bone fastener 712. In some embodiments, the washer 782 fits on the proximal portion 766 of the bone fastener 712.

In some embodiments, the spinal rod locking device 772 comprises a nut 754. In some embodiments, the nut 754 fits within the cavity 718 of the collar 724. In some embodiments, the nut 754 comprises a cam surface 716. The cam surface 716 may be on a distal portion 742 of the nut 754. In some embodiments, the cam surface 716 is adapted to impart distal force to a clamp member 720 of the spinal rod locking device 772. In some embodiments, the nut 754 is adapted to turn about an axis 704.

The nut 754 may comprise a collar engagement member 722. In some embodiments, the collar engagement member 722 is adapted to engage an inner surface of the collar 724. In some embodiments, the collar engagement member 722 is adapted to engage an outer surface of the collar 724. In some embodiments, the collar engagement member 722 is adapted to engage an overhang 726 in the collar 724. In the embodiment depicted in FIG. 7, the overhang 726 is on the inner surface of the collar 724. In some embodiments, the overhang 726 is on an outer surface of the collar 724. In some embodiments, the collar engagement member 722 is adapted to engage the overhang 726 to resist proximal motion of the nut 754, whereby force imparted by turning of the nut 754 about the axis 704 is directed distally. In some embodiments, the nut 754 is adapted to turn about an axis 704, and possesses a distal cam surface 754, which is adapted to impart distal force to a clamp member 720. In some embodiments, the collar engagement member 722 is adapted to cooperate with the non-cammed slot 760 to engage an overhang 726 of the collar 724 to resist proximal motion of the nut 754, whereby force imparted by turning of the nut 754 about the axis 704 is directed distally.

In some embodiments, the spinal rod locking device 772 comprises a clamp member 720 having a distal surface 744. The clamp member 720 may comprise a cam surface 714. The cam surface 714 may be on a proximal end 762 of the clamp member 720. In some embodiments, the cam surface 714 on the proximal end 762 of the clamp member 720 is adapted to engage or interact with the cam surface 716 on the distal portion 742 of the nut 754, whereby turning the nut 754 imparts distal force to the clamp member 720. In some embodiments, at least a portion of the distal surface 744 of the clamp member 720 is concave, convex, or planar. In some embodiments, at least a portion of the distal surface 44 of the clamp member 720 is concave. In some embodiments, the surface 744 is adapted to engage a surface 778 of a rod 770 extending through the wall aperture 758. In some embodiments, the planar, concave, or convex distal surface 44 is adapted to engage the rod 770 extending through the wall aperture 758. The rod 770 is shown in FIG. 7A and FIG. 7B having a substantially uniform cross-section 776. In some embodiments, the clamp member 720 possesses a concave distal surface 744. In some embodiments, the clamp member 720 possesses a proximal cam surface 714 which interacts with the distal cam surface 716 of the nut 754, and which is adapted to receive distal force from the nut 754 and impart distal force to a rod 770 extending through the wall aperture 758.

In some embodiments, the collar seat 786 comprises a beveled surface 706. In some embodiments, the beveled surface 6 faces the distal portion 740 of the collar 724. In some embodiments, the beveled surface 706 is planar, convex or concave frustoconical. In some embodiments, the beveled surface 706 is on a distal portion (not shown) of the collar seat 786. In some embodiments, the beveled surface 706 is on a proximal portion 790 of the collar seat 786.

In some embodiments, the bone attachment device 710 comprises a collar overhang 726 extending from a portion of the collar 724 toward the cavity 718.

Figure 8:
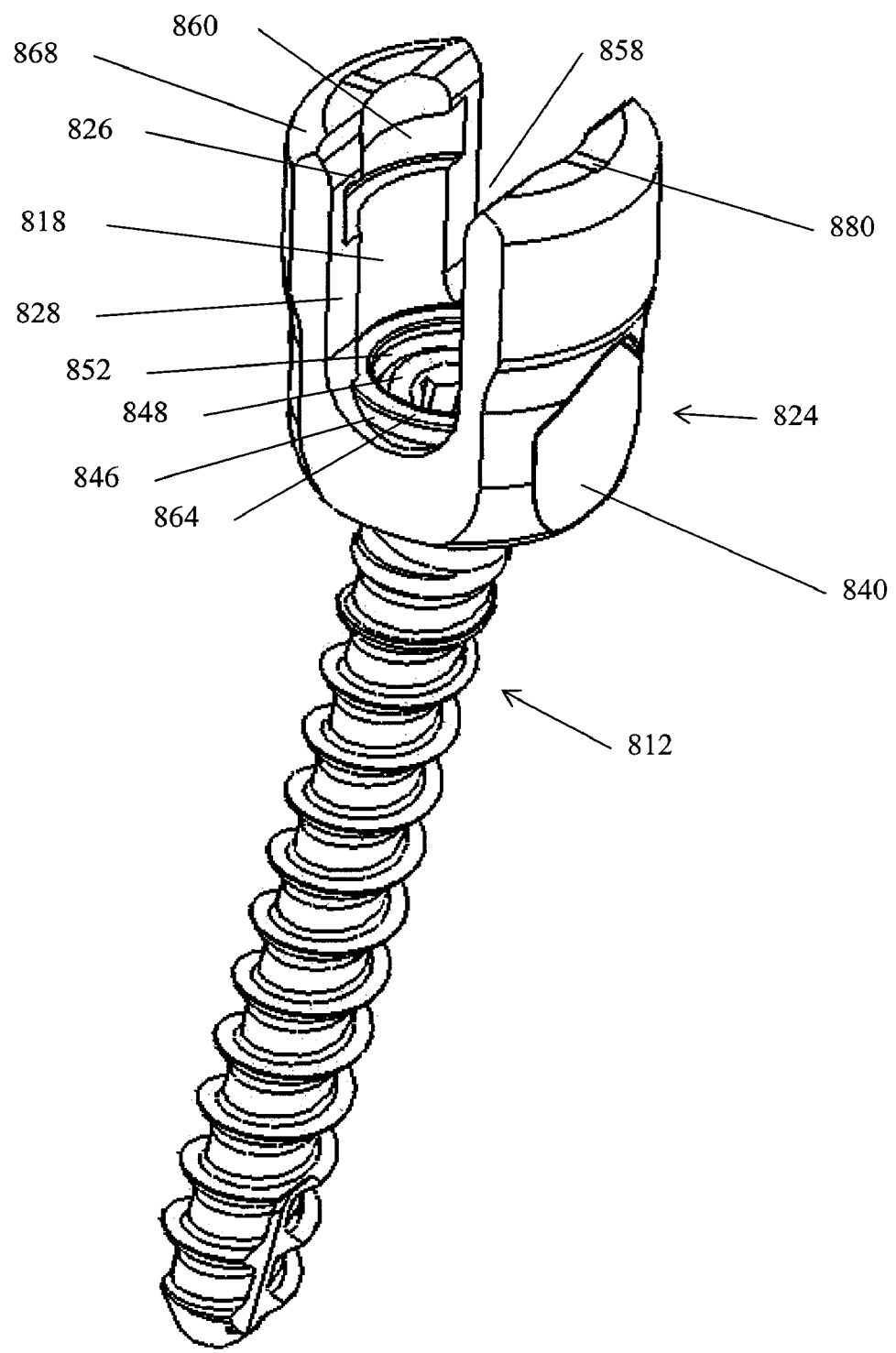
FIG. 8 shows an embodiment of a non-hinged bone attachment device including a bone attachment collar, washer and bone fastener.
Figure 9:
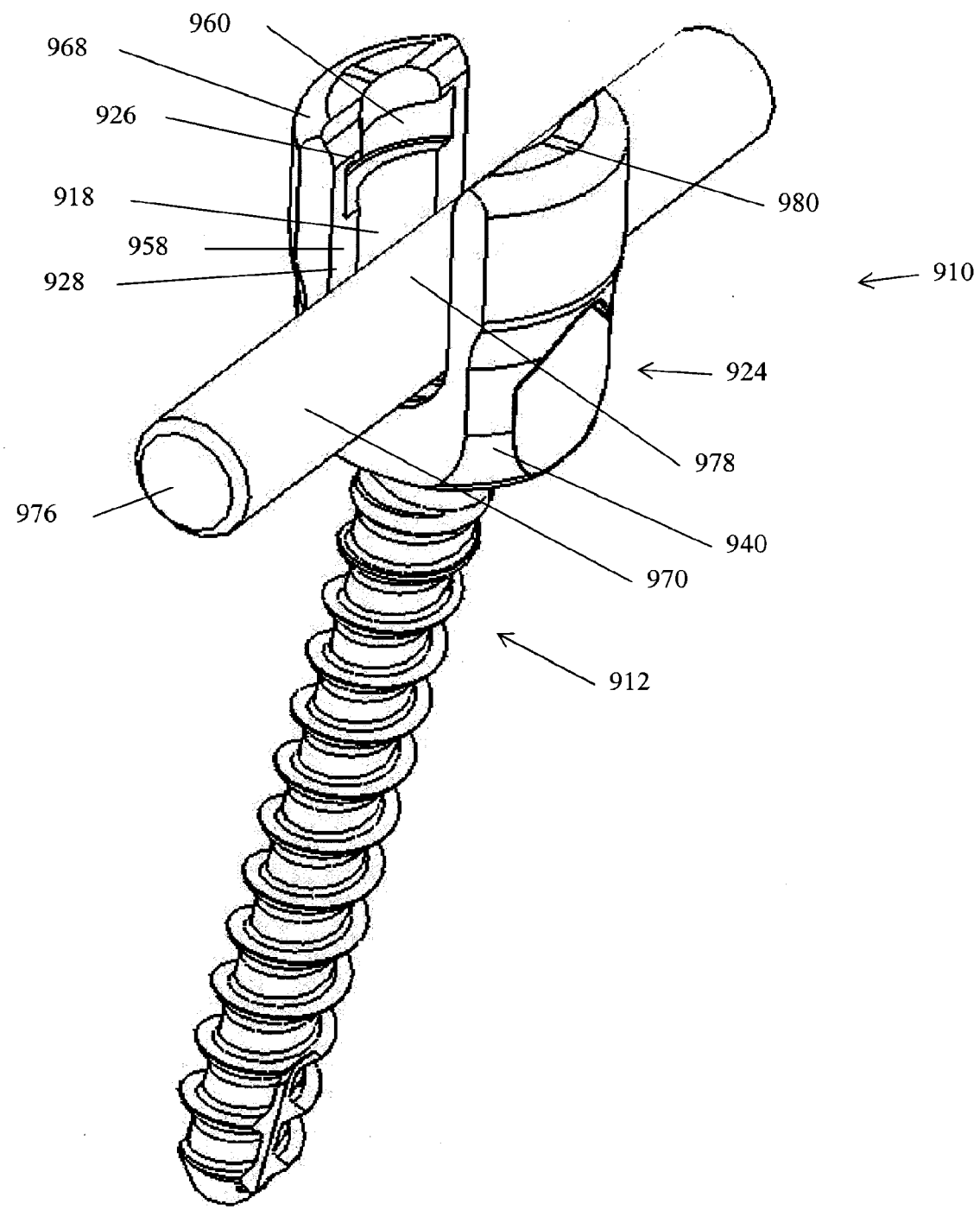
FIG. 9 shows an embodiment of a non-hinged bone attachment device including a bone attachment collar, a bone fastener and a stabilizing rod.
Figure 10:
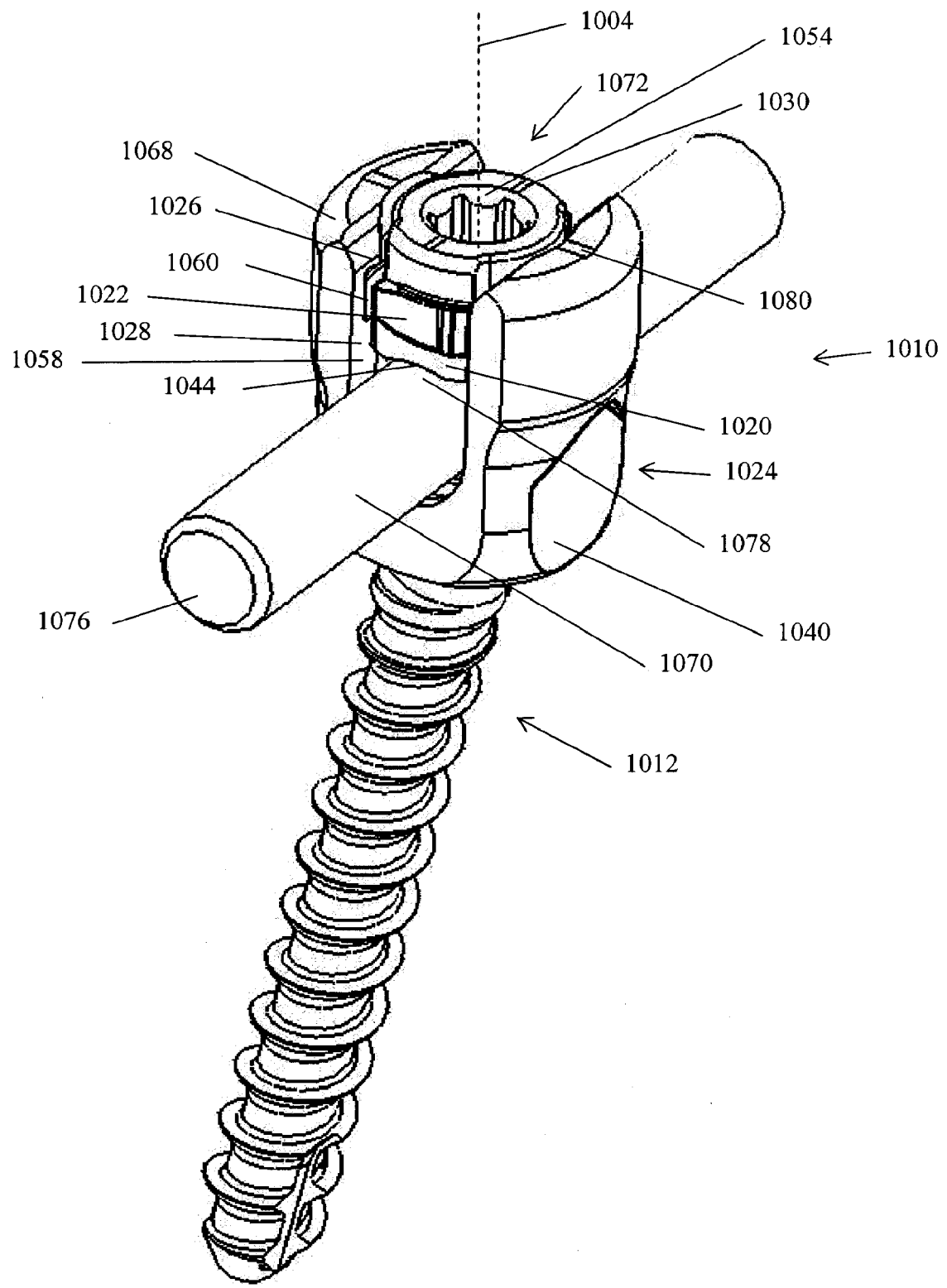
FIG. 10 shows an embodiment of a bone attachment device, which is unlocked and closed, and which includes a bone attachment collar, and a spinal rod locking device. A rod and a bone fastener are also depicted.

Each of the bone attachment device embodiments depicted in FIG. 7A-FIG. 13 can be assembled during surgery. For example, using elements shown in FIG. 7A-FIG. 13, a bone fastener 712 projecting through an opening 756 of a collar 724 is fastened to bone (e.g. the pedicle). Next, a washer 882, shown in FIG. 8, can be placed within the cavity 718 of the collar 724. Alternatively, the washer 882 may be placed within cavity 818 of the collar 824 prior to fastening the bone fastener 812 to bone. As depicted in FIG. 9, the rod 970 is then placed within the cavity 918 and through at least one aperture 902 of the collar 924. The rod 970 contacts at least a portion of the distal end (not shown) of the washer 982 (hidden by the rod in FIG. 9). In some embodiments, and as shown in FIG. 10, the spinal rod locking device 1072 is then assembled by placing a clamp member 1020 within the cavity 1018 of the collar 1024 and against the rod 1070. The nut 1054 can then be placed over the clamp member 1020 such that the collar engagement member 1022 of the nut 1054 is over the rod 1070, and such that the cam surface (not shown) of the clamp member 1020 faces the cam surface (not shown) of the nut 1054.

Alternatively, in some embodiments, the clamp member and the collar engagement member may be pre-assembled into a two-piece spinal locking device. The two piece spinal locking device (comprising the clamp member and the nut) can be placed simultaneously within the cavity of the collar, with the clamp member facing the rod and the collar engagement member over the rod. Alternatively, the clamp member can be pre-placed within the cavity of the collar, and the nut can then be placed within the cavity proximal to the clamp member. Once the nut and clamp member are within the cavity of the collar proximal to the rod, the nut can be turned such that the collar engagement member slides into the non-cammed slot of the collar. In some embodiments, the non-cammed slot and the overhang are on at least one of an inner surface of the collar and an outer surface of the collar. The collar engagement member engages the collar overhang to resist proximal motion of the nut as the nut is turned and the cam surface of the nut cams against the cam surface of the clamp member, thereby translating rotational motion of the nut into axial motion of at least the clamp member distally along the axis.

Depicted in FIG. 8 is an embodiment of a bone attachment device 810. With the spinal rod locking device (not shown) removed, the rod (not shown) can be placed into the cavity 818 defined by the collar wall 828 of the collar 824, and through at least one wall aperture 858 of the collar 824. Once placed into the cavity 818, the rod rests against the washer 882 at the washer proximal end 864 within the cavity 818 of the collar 824, which engages the head 848 of the bone fastener 812.

FIG. 8 also shows an embodiment of the bone attachment collar 824 having a distal portion 840, a proximal portion 868, and an overhang 826. In FIG. 8, the non-cammed slot 860 and the overhang 826 are on an inner surface of the collar. In some embodiments, the non-cammed slot 860 and the overhang 826 are on an outer surface of the collar 824. The overhang 826 can be used in conjunction with the spinal rod locking device to lock the rod against translation and into a fixed orientation relative to the bone fastener 812. In some embodiments, spinal rod locking device 872 of the bone attachment device 810 is adapted to lock the rod 870 in place, thereby preventing translational motion of the rod 870. In some embodiments, spinal rod locking device 872 of the bone attachment device 810 is adapted to lock the orientation of the bone fastener 812 relative to the rod 870 when the rod 870 is locked in place.

FIG. 9 shows a non-hinged bone attachment device including a bone attachment collar and a bone fastener, and including a rod. With the spinal rod locking device (not shown) removed, the rod 970 has been placed into the cavity 918 defined by the collar wall 928 of the collar 924, and through at least one wall aperture 958 of the collar 924. Once placed into the cavity 918, the rod rests against the washer (not shown, hidden by rod in this embodiment) at the washer proximal end 964 within the cavity 918 of the collar 924, which engages the head 948 of the bone fastener 912.

FIG. 9 also shows an embodiment of the bone attachment collar 924 having a distal portion 940, a proximal portion 968, a non-cammed slot 960 and an overhang 926. The overhang 926 and the non-cammed slot 960 can be used in conjunction with the spinal rod locking device to lock the rod 970 against translation and into a fixed orientation relative to the bone fastener 912. In FIG. 9, the non-cammed slot 960 and the overhang 926 are on an inner surface of the collar 924. In some embodiments, the non-cammed slot 960 and the overhang 926 are on an outer surface of the collar 924. In some embodiments, spinal rod locking device 972 of the bone attachment device 910 is adapted to lock the rod 970 in place, thereby preventing translational motion of the rod 970. In some embodiments, spinal rod locking device 972 of the bone attachment device 910 is adapted to lock the orientation of the bone fastener 912 relative to the rod 970 when the rod 970 is locked in place.

The spinal rod locking device 1072 depicted in FIG. 10 comprises a clamp member 1020 which is adapted to engage the surface of the rod 1070 when the bone attachment device 1010 is closed and unlocked, and/or closed and locked. At least a portion of the proximal end (not shown) of the clamp member 1020 engages the nut 1054. Both the nut 1054 and the clamp member 1020, in some embodiments, have cam surfaces (not shown), which face each other. The nut 1054, which is capable of rotating within the cavity 1018, also comprises a collar engagement member 1022 which is capable of engaging the collar overhang 1026 when the spinal rod locking device 1072 is closed and the nut 1054 is rotated. In FIG. 10, the non-cammed slot 1060 and the overhang 1026 are on an inner surface of the collar 1024. In some embodiments, the non-cammed slot 1060 and the overhang 1026 are on an outer surface of the collar 1024.

Depicted in FIG. 10 is a closed and unlocked embodiment of the bone attachment device 1010 including a rod 1070. The polyaxial nature of the bone fastener 1012 is shown as the bone fastener is not aligned with the axis 1004 about which the nut 1054 of the spinal rod locking device 1072 is adapted to turn. In this figure, the rod 1070 has been placed into the cavity 1018 defined by the collar wall 1028 of the collar 1024, and through at least one wall aperture 1058 of the collar 1024. The spinal rod locking device 1072 has been placed into the cavity 1018 over the rod 1070 and the clamp member 1020 engages the surface 1078 of the rod 1070, which has a substantially uniform cross-section 1076 (circular in the FIG. 10 embodiment). When the spinal rod locking device 1072 is closed and unlocked, the collar engagement member 1022 of the nut 1054, is over the rod 1070. In this embodiment, the nut 1054 can be rotated relative to the collar 1024 and relative to the clamp member 1020. In the unlocked position, the collar engagement member 1022 of the nut 1054 does not engage the collar overhang 1026. From the closed and unlocked position depicted in FIG. 10, the nut 1054 may be turned in a clockwise direction such that the nut engagement marking 1030 rotates to align with the collar engagement marking 1080. In the embodiment depicted in FIG. 10, the cam surfaces (not shown) of the nut 1054 and the clamp member 1020 are positioned and oriented such that clockwise rotation of the nut 1054 locks the bone attachment device 1010 and rod 1070.

In some embodiments, the nut can be turned counterclockwise to engage the non-cammed slot of the collar. In some embodiments, the collar engagement member, and the cam surfaces of the nut and the clamp member are positioned and oriented such that counter-clockwise rotation of the nut locks the bone attachment device and rod. In some embodiments, the collar comprises two non-cammed slots. The collar engagement marking and the nut engagement marking as shown in FIG. 10 ensures locking of the spinal rod locking device.

Figure 11:
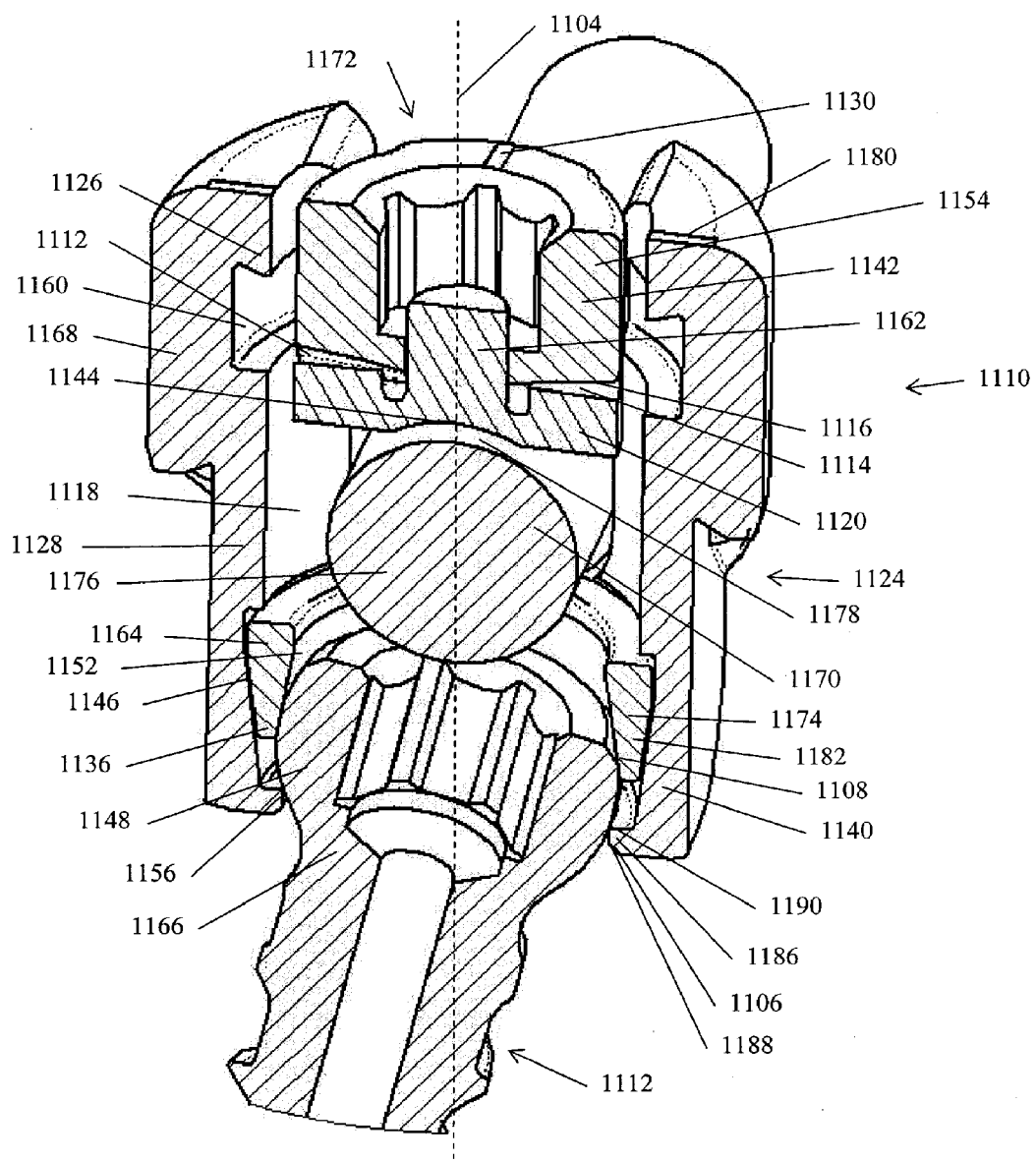
FIG. 11 shows a cross-section view of an embodiment of s bone attachment device of FIG. 10, which is closed and unlocked, including a rod.

Depicted in FIG. 11 is a cross-section view of the closed and unlocked embodiment of a bone attachment device of FIG. 10 including a rod. In this figure, bone fastener 1112 has been placed through the cavity 1118 of the collar 1124. The head 1148 of the bone fastener 1112 rests against the collar seat 1186. The washer 1182 has been placed against the head 1148 of the bone fastener 1112 and within the cavity 1118 of the collar 1124. The beveled surface 1108 of the distal end 1136 of the washer 1182 contacts the head 1148 of the bone fastener 1112. The polyaxial nature of the bone fastener 1112 is shown as the bone fastener is not aligned with the axis 1104 about which the nut 1154 of the spinal rod locking device 1172 is adapted to turn.

The rod 1170 has been placed into the cavity 1118 defined by the collar wall 1128 of the collar 1124, and through at least one wall aperture 1158 of the collar 1124. The rod 1170 rests on the washer 1182. The spinal rod locking device 1172 has been placed in the cavity 1118 of the collar 1124 and the clamp member 1120 engages the surface 1178 of the rod 1170, which has a substantially uniform cross-section 1176 (circular in the FIG. 11 embodiment). When the spinal rod locking device 1172 is closed and unlocked, the collar engagement member (not shown) of the nut 1154, is over the rod 1170. In this embodiment, the nut 1154 is within the cavity 1118 of the collar 1124, and can be rotated relative to the collar 1124 and relative to the clamp member 1120. In the unlocked position, the collar engagement member (not shown) of the nut 1154 does not engage the collar overhang 1126. In FIG. 11, the non-cammed slot 1160 and the overhang 1126 are on an inner surface of the collar 1124. In some embodiments, the non-cammed slot 1160 and the overhang 1126 are on an outer surface of the collar 1124. From the closed and unlocked position depicted in FIG. 11, the nut 1154 may be turned in a clockwise direction such that the nut engagement marking 1130 rotates to align with the hinged lid engagement marking 1132. In some embodiments, the collar engagement member 1122, and the cam surface 1112 of the nut 1154 and the cam surface 1114 of the clamp member 1120 are positioned and oriented such that clockwise rotation of the nut 1154 locks the bone attachment device 1110 and rod 1170. In the embodiment of FIG. 11, the cam surface 1112 of the nut 1154 and the cam surface 1114 of the clamp member 1120 face each other, such that when the nut 1154 is turned clockwise, rotation of the nut 1154 locks the bone attachment device 1110 and rod 1170.

In some embodiments, the collar engagement member 1122, and the cam surface 1112 of the nut 1154 and the cam surface 1114 of the clamp member 1120 are positioned and oriented such that counter-clockwise rotation of the nut 1154 locks the bone attachment device 1110 and rod 1170.

Figure 12:
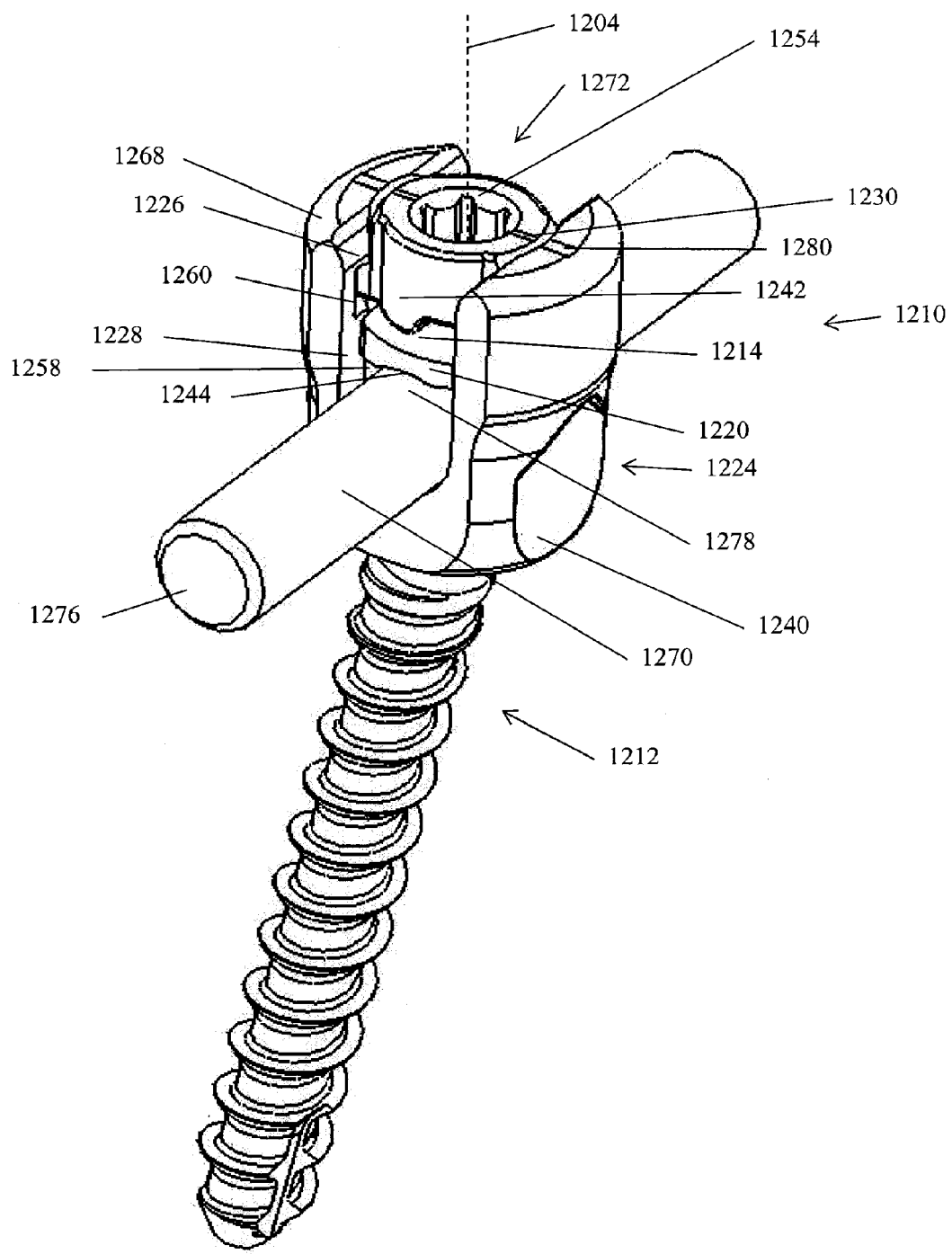
FIG. 12 shows an embodiment of a non-hinged bone attachment device, which is closed and locked, and which includes a bone attachment collar, and a spinal rod locking device, and including a rod and a bone fastener.

Depicted in FIG. 12 is a closed and locked embodiment of a bone attachment device 1210 including a rod 1270. In the closed and locked position, the rod 1270 has been placed into the cavity 1218 defined by the collar wall 1228 of the collar 1224, and through at least one wall aperture 1258 of the collar 1224. The spinal rod locking device 1272 has been placed into the cavity 1218 over the rod 1270 and the clamp member 1220 engages the surface 1278 of the rod 1270, which has a substantially uniform cross-section 1276 (circular in the FIG. 12 embodiment). The nut 1254 is within the cavity 1218, and has been rotated in a clockwise direction relative to the collar 1224 and relative to the clamp member 1220, such that the collar engagement member (not shown) of the nut 1254, engages at least one collar overhang 1226, and the cam surfaces (not shown) of the nut 1254 and the clamp member 1220 cam against one another. The rotational force of turning the nut 1254 about the axis 1204, translates rotational motion into axial motion, and moves at least the clamp member 1220 distally along axis 1204. This locks the rod 1270 from translation along its length and locks the position and orientation of the collar 1224 relative to the bone fastener 1212. In the embodiment shown in FIG. 12, the bone attachment device 1210 is fully locked at least when the nut 1254 is turned such that the nut engagement marking 1230 aligns with the collar engagement marking 1280. In FIG. 12, the non-cammed slot 1260 and the overhang 1226 are on an inner surface of the collar 1224. In some embodiments, the non-cammed slot 1260 and the overhang 1226 are on an outer surface of the collar 1224.

Figure 13:
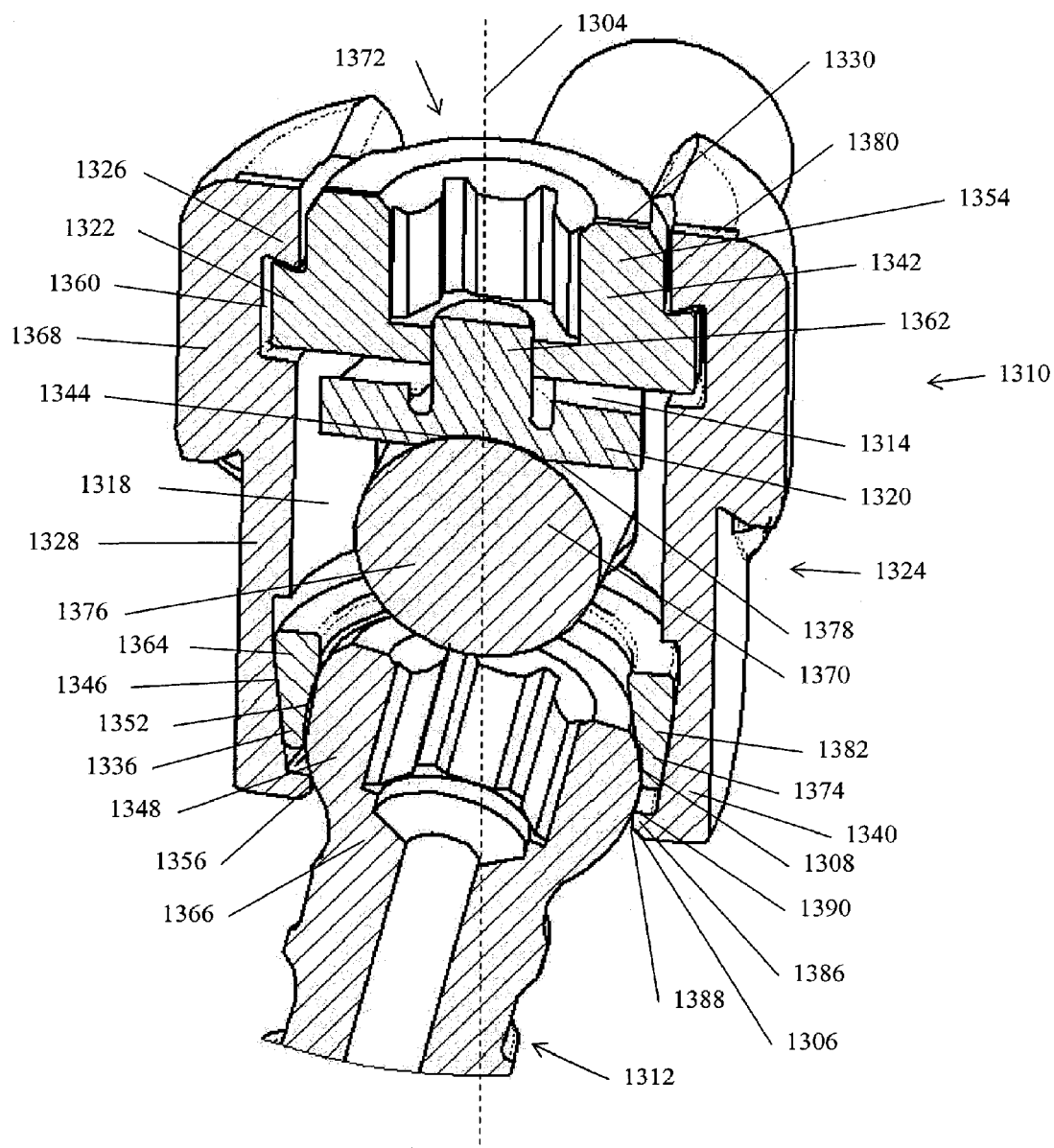
FIG. 13 depicts a cross-section view of the non-hinged bone attachment device of FIG. 12, which is closed and locked. A spinal stabilization rod is also depicted in this view.

FIG. 13 depicts a cross-section view of the closed and locked embodiment of the non-hinged bone attachment device of FIG. 12 including a rod. In this figure, bone fastener 1312 has been placed through the cavity 1318 of the collar 1324. The head 1348 of the bone fastener 1312 rests against the collar seat 1312. The washer 1382 has been placed against the head 1348 of the bone fastener 1312 and within the cavity 1318 of the collar 1324. The beveled surface 1308 of the distal end 1312 of the washer 1382 contacts the head 1348 of the bone fastener 1312. The rod 1370 has been placed into the cavity 1318 defined by the collar wall 1328 of the collar 1324, and through at least one wall aperture 1358 of the collar 1324. The rod 1370 rests on the washer 1382. The spinal rod locking device 1272 has been placed in the cavity 1318 over the rod 1370 and the clamp member 1320 engages the surface 1378 of the rod 1370, which has a substantially uniform cross-section 1312 (circular in the FIG. 13 embodiment).

In FIG. 13, the nut 1354 is within the cavity 1318 of the collar 1324, and has been rotated in a clockwise direction relative to the collar 1324 and relative to the clamp member 1320, such that the collar engagement member 1322 of the nut 1354 moves into the non-cammed slot 1360 and engages the collar overhang 1326, and the cam surface (not shown) of the nut 1354 and the cam surface 1314 of the clamp member 1320 cam against one another. The rotational force of turning the nut 1354 about the axis 1304, translates rotational motion into axial motion, and at least moves the clamp member 1320 distally along axis 1304. This locks the rod 1370 from translation along its length and locks the position and orientation of the collar 1324 relative to the bone fastener 1312. In the embodiment shown in FIG. 13, the bone attachment device 1310 is sufficiently locked at least when the nut 1354 is turned such that the nut engagement marking 1330 aligns with the collar engagement marking 1380. In FIG. 13, the non-cammed slot 1360 and the overhang 1326 are on an inner surface of the collar 1324. In some embodiments, the non-cammed slot 1360 and the overhang 1326 are on an outer surface of the collar 1324.

Provided herein and depicted in FIG. 1A through FIG. 13 are embodiments of a bone attachment collar comprising a collar wall defining a cavity and having at least one wall aperture. In some embodiments, the bone attachment collar comprises a distal portion comprising an opening and a collar seat projecting inward and supporting the head of the bone fastener. In some embodiments, the bone attachment collar comprises a proximal portion having a hinged lid, an example of which is shown in FIG. 5. Other embodiments of the bone attachment collar do not have a hinged lid, an example of which is shown in FIG. 12. In some embodiments, the collar comprises a proximal portion having a non-cammed slot. In some embodiments, the collar comprises a proximal portion having at least two non-cammed slots. In some embodiments, the non-cammed slots and the overhangs are on an inner surface of the collar. In some embodiments, the non-cammed slots and the overhangs are on an outer surface of the collar. In such an embodiment, the slots are on opposite sides of the cavity. In some embodiments, the bone attachment collar comprises a spinal rod locking device, wherein at least a portion of the spinal locking device is within the cavity defined by the collar wall.

In some embodiments, the bone attachment collar comprises a washer as described herein, and shown in embodiments depicted in FIGS. 1A, 1B, 4, 6, 7A, 7B, 8, 11, 13. The washer has a proximal end and a distal end. The washer may comprise a substantially cylindrical wall having an interior surface and an exterior surface. In some embodiments, the distal end of the washer fits over the head of the bone fastener. The washer may comprise a beveled surface. FIG. 4 shows an example of the beveled surface 408 of the washer 482. The beveled surface may be on the distal end of the washer. The beveled surface may be on the interior surface of the cylindrical wall. The beveled surface may be, for non-limiting example, concave, convex or planar. In some embodiments, the beveled surface is planar frustoconical. In some embodiments, the beveled surface abuts a proximal portion of the bone fastener. In some embodiments, the washer fits on the proximal portion of the bone fastener.

In some embodiments, the bone attachment collar comprises a nut as described herein and as shown, for example, in FIGS. 1A, 1B, 2, 3, 4, 5, 6, 7A, 7B, 11, 13. The nut may project through an aperture of the hinged lid of the bone attachment collar, for example, as shown in FIG. 4. In some embodiments, the nut may project through an aperture of the proximal portion of the bone attachment collar. In some embodiments, the nut may fit within the cavity of the collar, for example, as shown in FIG. 11 or FIG. 13. In some embodiments, the nut comprises a cam surface. The cam surface may be on a distal portion of the nut. In some embodiments, the distal cam surface is adapted to impart distal force to a clamp member of the spinal rod locking device. In some embodiments, the nut is adapted to turn about an axis.

The nut may comprise a collar engagement member, for example, as shown in FIGS. 1A, 1B, 2, 3, 6, 7A, 7B, 10, 13, and as described herein. In some embodiments, the collar engagement member is adapted to engage an inner surface of the collar. In some embodiments, the collar engagement member is adapted to engage an outer surface of the collar. In some embodiments, the collar engagement member is adapted to engage an overhang in the collar. In some embodiments, the overhang comprises an inclined surface. In some embodiments, the collar engagement member is adapted to engage the overhang to resist proximal motion of the nut, whereby force imparted by turning of the nut about the axis is directed distally. In some embodiments, the nut is adapted to turn about an axis, and possesses a distal cam surface, which is adapted to impart distal force to a clamp member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on an inner surface of the collar. In some embodiments, the non-cammed slot and the overhang are on an outer surface of the collar.

In some embodiments, the spinal rod locking device comprises a clamp member having a distal surface. Embodiments of the clamp member are shown, for example, in FIGS. 1A, 1B, 2, 3, 4, 5, 6, 7A, 7B, 10, 11, 12, 13. The clamp member may comprise a cam surface. The cam surface may be on a proximal end of the clamp member. In some embodiments, the cam surface on the proximal end of the clamp member is adapted to engage or interact with the cam surface on the distal portion of the nut, whereby turning the nut imparts distal force to the clamp member. In some embodiments, at least a portion of the distal surface of the clamp member is concave, convex, or planar. In some embodiments, at least a portion of the distal surface of the clamp member is concave. In some embodiments, the surface is adapted to engage a surface of a rod extending through the wall aperture. The rod 70 is shown, as a non-limiting example, in FIG. 1A and FIG. 1B, having a substantially uniform cross-section 76. In some embodiments, the planar, concave, or convex distal surface is adapted to engage the rod extending through the wall aperture. In some embodiments, the clamp member possesses a concave distal surface. In some embodiments, the clamp member possesses a proximal cam surface which interacts with the distal cam surface of the nut, and which is adapted to receive distal force from the nut and impart distal force to a rod extending through the wall aperture.

In some embodiments, the collar comprises a collar seat, for example, as shown in FIGS. 1B, 4, 6, 7B, 11, 13. The collar seat may comprise a beveled surface. In some embodiments, the beveled surface faces the distal portion of the collar. In some embodiments, the beveled surface is planar, convex or concave frustoconical. In some embodiments, the beveled surface is on a distal portion of the collar seat. In some embodiments, the beveled surface is on a proximal portion of the collar seat.

In some embodiments, the bone attachment collar comprises a collar overhang extending from a portion of the collar toward the cavity. Examples of collar overhangs are depicted in FIGS. 1A, through 13.

Provided herein is a spinal stabilizer comprising at least two bone attachment devices as described herein and depicted in FIGS. 1A through 13, and a bone stabilization rod extending through the wall apertures of at least two bone attachment devices. The bone attachment devices are adapted to lock the rod in place, thereby preventing translational motion of the rod. In some embodiments, spinal rod locking devices of the bone attachment devices are adapted to lock the rod in place, thereby preventing translational motion of the rod. In some embodiments, spinal rod locking devices of the bone attachment devices are adapted to lock the orientation of the bone fastener relative to the rod when the rod is locked in place.

In some embodiments of the spinal stabilizer, at least one of, or both of the two bone attachment devices comprise a bone fastener having a distal portion adapted to pierce bone and a proximal portion having a head. For example, bone fasteners are shown in FIGS. 1A through 13. In some embodiments, the bone attachment device comprises a bone hook, whereby the bone hook attaches to the spinal segment by hooking a portion of the segment. At least one of, or both of, the two bone attachment devices may comprise a collar as described herein and shown in FIGS. 1A through 13. The collar may comprise a collar wall defining a cavity and having at least one wall aperture. The collar may comprise a distal portion comprising an opening and a collar seat projecting inward and supporting the head of the bone fastener. In some embodiments of the spinal stabilizer, the proximal portion of at least one of the two bone attachment devices may have a hinged lid and a spinal rod locking device, an example of which is shown in FIG. 5, wherein at least a portion of the spinal rod locking device is within the cavity defined by the collar wall. In some embodiments, the collar comprises a proximal portion having a non-cammed slot and a spinal rod locking device, an example of which is shown in FIG. 12, wherein at least a portion of the spinal rod locking device is within the cavity defined by the collar wall. In some embodiments of the spinal stabilizer, at least one of, or both of the two bone attachment devices comprises an opening and a collar seat projecting inward and supporting the head of the bone fastener, and a spinal rod locking device.

In some embodiments, the rod has a substantially uniform cross section. In some embodiments, the cross section is at least one of circular, elliptical, and polygonal. In some embodiments, the cross section is polygonal. As non-limiting examples, the polygonal cross section may be at least one of triangular, quadrangular (e.g. square, rectangular, rhomboidal, trapezoidal), pentagonal, hexagonal, heptagonal, and an octagonal shape.

In some embodiments, at least one bone attachment device of the spinal stabilizer comprises a washer as described herein, and shown in embodiments depicted in FIGS. 1A, 1B, 4, 6, 7A, 7B, 8, 11, 13. The washer has a proximal end and a distal end. The washer may comprise a substantially cylindrical wall having an interior surface and an exterior surface. In some embodiments, the distal end of the washer fits over the head of the bone fastener. The washer may comprise a beveled surface. FIG. 4 shows an example of the beveled surface 408 of the washer 482. The beveled surface may be on the distal end of the washer. The beveled surface may be on the interior surface of the cylindrical wall, in some embodiments. The beveled surface may be concave, convex or planar. In some embodiments, the beveled surface is planar frustoconical. In some embodiments, the beveled surface abuts a proximal portion of the bone fastener. In some embodiments, the washer fits on the proximal portion of the bone fastener.

In some embodiments, the at least one spinal rod locking device bone attachment device of the spinal stabilizer comprises a nut as described herein and as shown, for example, in FIGS. 1A, 1B, 2, 3, 4, 5, 6, 7A, 7B, 11, and 13. In some embodiments, the nut may project through an aperture of the hinged lid of the bone attachment device, for example, as shown in FIG. 4. In some embodiments, the nut may project through an aperture of the proximal portion of the bone attachment device. In some embodiments, the nut may fit within the cavity of the collar, for example, as shown in FIG. 11 or FIG. 13. In some embodiments, the nut comprises a cam surface. The cam surface may be on a distal portion of the nut. In some embodiments, the distal cam surface is adapted to impart distal force to a clamp member of the spinal rod locking device. In some embodiments, the nut is adapted to turn about an axis.

In some embodiments, the at least one spinal rod locking device bone attachment device of the spinal stabilizer comprises a nut comprising a collar engagement member, for example, as shown in FIGS. 1A, 1B, 2, 3, 6, 7A, 7B, 10, and 13, and as described herein. In some embodiments, the collar engagement member is adapted to engage an overhang in the collar. In some embodiments, the overhang comprises an inclined surface. In some embodiments, the collar engagement member is adapted to engage the overhang to resist proximal motion of the nut, whereby force imparted by turning of the nut about the axis is directed distally. In some embodiments, the nut is adapted to turn about an axis, and possesses a distal cam surface, which is adapted to impart distal force to a clamp member. In some embodiments, the collar engagement member is adapted to cooperate with the non-cammed slot to engage an overhang of the collar to resist proximal motion of the nut, whereby force imparted by turning of the nut about the axis is directed distally. In some embodiments, the non-cammed slot and the overhang are on an inner surface of the collar. In some embodiments, the non-cammed slot and the overhang are on an outer surface of the collar.

In some embodiments, the spinal rod locking device of at least one spinal stabilizer comprises a clamp member having a distal surface. Embodiments of the clamp member are shown, for example, in FIGS. 1A, 1B, 2, 3, 4, 5, 6, 7A, 7B, 10, 11, 12, and 13. The clamp member may comprise a cam surface. The cam surface may be on a proximal end of the clamp member. In some embodiments, the cam surface on the proximal end of the clamp member is adapted to engage or interact with the cam surface on the distal portion of the nut, whereby turning the nut imparts distal force to the clamp member. In some embodiments, at least a portion of the distal surface of the clamp member is concave, convex, or planar. In some embodiments, at least a portion of the distal surface of the clamp member is concave. In some embodiments, the surface is adapted to engage a surface of a rod extending through the wall aperture. The rod 70 is shown, as a non-limiting example, in FIG. 1A and FIG. 1B, having a substantially uniform cross-section 76. In some embodiments, the planar, concave, or convex distal surface is adapted to engage the rod extending through the wall aperture. In some embodiments, the clamp member possesses a concave distal surface. In some embodiments, the clamp member possesses a proximal cam surface which interacts with the distal cam surface of the nut, and which is adapted to receive distal force from the nut and impart distal force to a rod extending through the wall aperture.

In some embodiments, the collar of at least one bone attachment device of the spinal stabilizer comprises a collar seat, for example, as shown in FIGS. 1B, 4, 6, 7B, 11, 13. The collar seat may comprise a beveled surface. In some embodiments, the beveled surface faces the distal portion of the collar. In some embodiments, the beveled surface is planar, convex or concave frustoconical. In some embodiments, the beveled surface is on a distal portion of the collar seat. In some embodiments, the beveled surface is on a proximal portion of the collar seat.

In some embodiments, at least one bone attachment device of the spinal stabilizer comprises a collar overhang extending from a portion of the collar toward the cavity. Examples of collar overhangs are depicted in FIGS. 1A, through 13.

Provided herein is a method for implanting a spinal stabilization device comprising delivering a first bone attachment device to a first pedicle, wherein the first bone attachment device comprises a first bone fastener having a distal portion adapted to pierce bone and a proximal portion having a head, and a first collar comprising a collar wall defining a cavity and having at least one wall aperture, a distal portion comprising an opening and a collar seat projecting inward and supporting a head of the bone fastener, a proximal portion having a hinged lid, and a spinal rod locking device, wherein at least a portion of the spinal rod locking device is within the cavity defined by the collar wall. The method may further comprise fastening the distal portion of the first bone fastener to the first pedicle. In some embodiments, the method comprises delivering a second bone attachment device to a second pedicle, wherein the second bone attachment device comprises a second bone fastener having a distal portion adapted to pierce bone and a proximal portion having a head, and a second collar comprising: a collar wall defining a cavity and having at least one wall aperture; a distal portion comprising an opening and a collar seat projecting inward and supporting a head of the bone fastener; and a spinal rod locking device, wherein at least a portion of the spinal rod locking device is within the cavity defined by the collar wall. In some embodiments, the method comprises placing a rod within the aperture of the first bone attachment device. The method may further comprise placing the rod within the aperture of the second bone attachment device. In some embodiments, the method further comprises locking the first bone attachment device, wherein the locking comprises pivoting the hinged lid toward the first collar over the rod, and engaging an overhang of the first collar with a collar engagement member of the spinal rod locking device of the first collar. The method may further comprise locking the second bone attachment device. The locking steps may lock the rod in place, thereby preventing translational motion of the rod.

In some embodiments, the second collar of the second bone attachment device comprises a proximal portion having a hinged lid. In some embodiments of the method, locking the second bone attachment device comprises: pivoting the hinged lid toward the first collar over the rod; and engaging an overhang of the first collar with a collar engagement member of the spinal rod locking device of the first collar.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A bone attachment device, comprising:
   (a) a bone fastener having a distal portion adapted to pierce bone and a proximal portion having a head;
   (b) a collar comprising:
      (i) a collar wall defining a cavity and having at least one wall aperture;
      (ii) a distal portion comprising an opening and a collar seat projecting inward and supporting the head of the bone fastener;
      (iii) a proximal portion having a hinged lid attached to the collar wall with a pivot pin, the hinged lid possessing a central aperture and a lid hook opposite the pivot in wherein the lid hook is adapted to engage a corresponding feature in the collar wall; and
      (iv) a spinal rod locking device passing through the central aperture in the hinged lid, comprising:
         (A) a nut, the nut having an outer diameter, the nut being adapted to turn about an axis from an unlocked configuration to a locked configuration, and which possesses a distal cam surface and a collar engagement member projecting radially from only a segment of an outer diameter surface of the nut such that the collar engagement member does not extend around the entire outer diameter of the nut, wherein the distal cam surface is adapted to impart distal force to a clamp member and the collar engagement member is adapted to rotatably engage a collar overhang of the collar wall in the locked configuration and not engage the collar wall in the unlocked configuration; and (B) the clamp member possessing a proximal cam surface, which interacts with the distal cam surface of the nut, and which is adapted to receive distal force from the nut and impart distal force to a rod extending through the at least one wall aperture;

wherein at least a portion of the spinal rod locking device is within the cavity defined by the collar wall.

2. The bone attachment device of claim 1, further comprising a washer.

3. The bone attachment device of claim 2, wherein the washer comprises a substantially cylindrical wall having an interior surface and an exterior surface; and the washer has a proximal end and a distal end.

4. The bone attachment device of claim 3, wherein the distal end of the washer fits over the head of the bone fastener.

5. The bone attachment device of claim 1, further comprising:

a washer having a beveled surface at a distal end of the washer, wherein the beveled surface abuts the proximal portion of the bone fastener, wherein the clamp member further comprises a distal surface, at least a portion of which is planar, convex or concave, and is adapted to engage the rod extending through the at least one wall aperture.

6. The bone attachment device of claim 1, further comprising:

(b) a washer having a beveled surface at a distal end of the washer, wherein the beveled surface abuts the proximal portion of the bone fastener, wherein the beveled surface is planar frustoconical, wherein the clamp member further comprises a distal surface, at least a portion of which is concave, and is adapted to engage the rod extending through the at least one wall aperture.

7. A spinal stabilizer, comprising:

(a) at least two bone attachment devices, each of the at least two bone attachment devices comprising:

(i) a bone fastener having a distal portion adapted to pierce bone and a proximal portion having a head; and (ii) a collar comprising (A) a collar wall defining a cavity and having at least one wall aperture, (B) a distal portion comprising an opening and a collar seat projecting inward and supporting the head of the bone fastener, (C) a proximal portion having a hinged lid attached to the collar wall with a pivot pin, the hinged lid possessing a central aperture and a lid hook opposite the pivot pin wherein the lid hook is adapted to engage a corresponding feature in the collar wall; and (D) a spinal rod locking device passing through the central aperture in the hinged lid, comprising:

(1) a nut, the nut having an outer diameter, the nut being adapted to turn about an axis from an unlocked configuration to a locked configuration, and which possesses a distal cam surface and a collar engagement member projecting radially from only a segment of an outer diameter surface of the nut such that the collar engagement member does not extend around the entire outer diameter of the nut, wherein the distal cam surface is adapted to impart distal force to a clamp member and the collar engagement member is adapted to rotatably engage a collar overhang of the collar wall in the locked configuration and not engage the collar wall in the unlocked configuration; and (2) the clamp member possessing a proximal cam surface, which interacts with the distal cam surface of the nut, and which is adapted to receive distal force from the nut;

wherein at least a portion of the spinal rod locking device is within the cavity defined by the collar wall; and (b) a bone stabilization rod extending through the at least one wall aperture of each of the at least two bone attachment devices;

wherein the clamp member of each of the at least two bone attachment devices imparts a distal force to the bone stabilization rod; and wherein the spinal rod locking devices are adapted to lock the bone stabilization rod in place, thereby preventing translational motion of the bone stabilization rod.

8. The spinal stabilizer of claim 7, further comprising a washer.

9. The spinal stabilizer of claim 7, wherein each of the bone attachment devices further comprises:

a washer having a beveled surface at a distal end of the washer, wherein the beveled surface abuts the proximal portion of the bone fastener, wherein the clamp member further comprises a distal surface, at least a portion of which is planar, convex or concave, and is adapted to engage the bone stabilization rod extending through the at least one wall aperture.

10. The spinal stabilizer of claim 7, wherein each of the bone attachment devices further comprises:

a washer having a beveled surface at a distal end of the washer, wherein the beveled surface abuts the proximal portion of the bone fastener, wherein the beveled surface is planar frustoconical, wherein the clamp member further comprises a distal surface, at least a portion of which is concave, and is adapted to engage the bone stabilization rod extending through the at least one wall aperture.

11. A bone attachment collar, comprising:

(a) a collar wall defining a cavity and having at least one wall aperture;

(b) a distal portion comprising an opening and a collar seat projecting inward and supporting a head of a bone fastener;

(c) a proximal portion having a hinged lid attached to the collar wall with a pivot pin, the hinged lid possessing a central aperture and a lid hook opposite the the pivot pin wherein the lid hook is adapted to engage a corresponding feature in the collar wall; and (d) a spinal rod locking device located at least partially within the central aperture in the hinged lid, comprising:

(i) a nut, the nut having an outer diameter, the nut being adapted to turn about an axis from an unlocked configuration to a locked configuration, and which possesses a distal cam surface and a collar engagement member projecting radially from only a segment of an outer diameter surface of the nut such that the collar engagement member does not extend around the entire outer diameter of the nut, wherein the distal cam surface is adapted to impart distal force to a clamp member and the collar engagement member is adapted to rotatably engage a collar overhang of the collar wall in the locked configuration and not engage the collar wall in the unlocked configuration; and (ii) the clamp member possessing a proximal cam surface, which interacts with the distal cam surface of the nut, and which is adapted to receive distal force from the nut and impart distal force to a rod extending through the at least one wall aperture; wherein at least a portion of the spinal locking device is within the cavity defined by the collar wall.

12. The bone attachment collar of claim 11, further comprising a washer.

13. The bone attachment collar of claim 11, further comprising:
   a washer having a beveled surface at a distal end of the washer, wherein the beveled surface abuts the head of the bone fastener, and
   wherein the clamp member further comprises a distal surface, at least a portion of which is planar, convex or concave, and is adapted to engage the rod extending through the at least one wall aperture.

14. The bone attachment collar of claim 11, further comprising:
   a washer having a beveled surface at a distal end of the washer, wherein the beveled surface abuts the head of the bone fastener, wherein the beveled surface is planar frustoconical; and
   wherein the clamp member further comprises a distal surface, at least a portion of which is concave, and is adapted to engage the rod extending through the at least one wall aperture.

* * * * *

UNITED STATES PATENT AND TRADEMARK OFFICE
CERTIFICATE OF CORRECTION

| | | |
|---|---|---|
| PATENT NO. | : 8,888,820 B2 | Page 1 of 1 |
| APPLICATION NO. | : 12/147159 | |
| DATED | : November 18, 2014 | |
| INVENTOR(S) | : Jason Daniel Blain | |

It is certified that error appears in the above-identified patent and that said Letters Patent is hereby corrected as shown below:

In the Claims

In column 44 at line 61, In Claim 1, change "in" to --pin--.

In column 46 at line 61, In Claim 11, change "the the" to --the--.

Signed and Sealed this
Twenty-third Day of June, 2015

Michelle K. Lee
*Director of the United States Patent and Trademark Office*